(12) United States Patent
Corey et al.

(10) Patent No.: US 8,901,095 B2
(45) Date of Patent: Dec. 2, 2014

(54) SELECTIVE INHIBITION OF POLYGLUTAMINE PROTEIN EXPRESSION

(75) Inventors: David R. Corey, Dallas, TX (US); Jiaxin Hu, Coppell, TX (US); Masayuki Matsui, Irving, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 502 days.

(21) Appl. No.: 13/056,556

(22) PCT Filed: Jul. 28, 2009

(86) PCT No.: PCT/US2009/051938
§ 371 (c)(1),
(2), (4) Date: Apr. 18, 2011

(87) PCT Pub. No.: WO2010/014592
PCT Pub. Date: Feb. 4, 2010

(65) Prior Publication Data
US 2011/0190222 A1    Aug. 4, 2011

Related U.S. Application Data

(60) Provisional application No. 61/084,350, filed on Jul. 29, 2008.

(51) Int. Cl.
*A61K 48/00* (2006.01)
*C07H 21/02* (2006.01)
*C07H 21/04* (2006.01)

(52) U.S. Cl.
USPC ........ 514/44; 536/23.1; 536/24.3; 536/24.31; 536/24.33; 536/24.5

(58) Field of Classification Search
None
See application file for complete search history.

(56) References Cited

U.S. PATENT DOCUMENTS

| | | | |
|---|---|---|---|
| 5,595,756 A | 1/1997 | Bally et al. | |
| 5,700,922 A | 12/1997 | Cook | |
| 5,801,154 A | 9/1998 | Baracchini et al. | |
| 5,998,148 A | 12/1999 | Bennett et al. | |
| 6,043,060 A | 3/2000 | Imanishi | |
| 6,147,200 A | 11/2000 | Manoharan et al. | |
| 6,582,908 B2 | 6/2003 | Fodor et al. | |
| 6,670,461 B1 | 12/2003 | Nielsen et al. | |
| 7,250,289 B2 | 7/2007 | Zhou | |
| 7,320,965 B2 | 1/2008 | Sah et al. | |
| 7,951,934 B2 | 5/2011 | Freier | |
| 8,415,465 B2 | 4/2013 | Freier | |
| 2001/0053519 A1 | 12/2001 | Fodor et al. | |
| 2002/0009752 A1 | 1/2002 | Burke et al. | 435/7.1 |
| 2003/0109476 A1 | 6/2003 | Kmiec et al. | 514/44 |
| 2003/0144242 A1 | 7/2003 | Ward et al. | |
| 2003/0228597 A1 | 12/2003 | Cowsert et al. | |
| 2003/0229019 A1 | 12/2003 | Burke et al. | 514/12 |
| 2004/0092465 A1 | 5/2004 | Dobie | |
| 2004/0096880 A1 | 5/2004 | Kmiec et al. | |
| 2004/0137471 A1 | 7/2004 | Vickers et al. | |
| 2005/0042646 A1 | 2/2005 | Davidson et al. | 435/6 |
| 2005/0096284 A1 | 5/2005 | McSwiggen | |
| 2005/0191638 A1 | 9/2005 | McSwiggen | |
| 2005/0255086 A1 | 11/2005 | Davidson | |
| 2005/0255487 A1 | 11/2005 | Khvorova et al. | |
| 2006/0003322 A1 | 1/2006 | Bentwich | |
| 2006/0051769 A1 | 3/2006 | Barts | |
| 2007/0031844 A1 | 2/2007 | Khvorova et al. | |
| 2007/0099860 A1 | 5/2007 | Sah et al. | |
| 2007/0111963 A1 | 5/2007 | Corey et al. | 514/44 |
| 2007/0161591 A1 | 7/2007 | Aronin et al. | 514/44 |
| 2007/0299027 A1 | 12/2007 | Hung et al. | |
| 2008/0015158 A1 | 1/2008 | Ichiro et al. | 514/44 |
| 2008/0039418 A1 | 2/2008 | Freier | |
| 2008/0274989 A1 | 11/2008 | Davidson et al. | |
| 2009/0092981 A1 | 4/2009 | Swayze et al. | |
| 2010/0069472 A1 | 3/2010 | Hung et al. | |
| 2012/0252879 A1 | 10/2012 | Hung et al. | |
| 2013/0189782 A1 | 7/2013 | Hung et al. | |
| 2013/0281684 A1 | 10/2013 | Freier | |

FOREIGN PATENT DOCUMENTS

| | | |
|---|---|---|
| WO | WO 94/26764 | 11/1994 |
| WO | WO 01/79283 | 10/2001 |
| WO | WO 03/013437 | 2/2003 |
| WO | WO 03/064625 | 8/2003 |
| WO | WO 2004/013280 | 2/2004 |
| WO | WO 2004/048601 | 6/2004 |
| WO | WO 2004/101787 | 11/2004 |
| WO | WO 2005/027980 | 3/2005 |
| WO | WO 2005/045032 | 5/2005 |
| WO | WO 2005/105995 | 11/2005 |
| WO | WO 2005/116204 | 12/2005 |
| WO | WO 2007/022470 | 2/2007 |
| WO | WO 2007/089584 | 8/2007 |
| WO | WO 2007/089611 | 8/2007 |
| WO | WO 2008/018795 | 2/2008 |
| WO | WO 2011/032045 | 3/2011 |
| WO | WO 2011/097388 | 8/2011 |

OTHER PUBLICATIONS

Boado et al., "Antisense-mediated down-regulation of the human huntingtin gene," *J. Pharmacol. Exp. Ther.*, 295:239-243, 2000.

(Continued)

*Primary Examiner* — Amy Bowman
(74) *Attorney, Agent, or Firm* — Parker Highlander PLLC

(57) ABSTRACT

The present invention relates to the selective inhibition of protein expression of CAG repeat-related disease proteins such as Huntingtin using nucleic acid analogs. Peptide nucleic acids and locked nucleic acids are particularly useful analogs.

27 Claims, 12 Drawing Sheets

(56) References Cited

OTHER PUBLICATIONS

Boffa et al., "Invasion of the CAG triplet repeats by a complementary peptide nucleic acid inhibits transcription of the androgen receptor and TATA-binding protein genes and correlates with refolding of an active nucleosome containing a unique AR gene sequence,", *J Biol Chem.*, 271(22):13228-13233, 1996.

Corey, "RNA learns from antisense," *Nat. Chem. Biol.*, 3:8-11, 2007.

Denovan-Wright and Davidson, "RNAi: a potential therapy for the dominantly inherited nucleotide repeat diseases," *Gene Therapy*, 13:525-531, 2006.

DiFiglia et al., "Therapeutic silencing of mutant huntingtin with siRNA attenuates striatal and cortical neuropathology and behavioral deficits," *Proc. Natl. Acad. Sci. USA*, 104:17204-17209, 2007.

Fiszer et al., "Inhibition of mutant huntingtin expression by RNA duplex targeting expanded CAG repeats," *Nucleic Acids Research* 1-8, 2011.

Gagnon et al., "Allele-selective inhibition of mutant huntingtin expression with antisense oligonucleotides targeting the expanded CAG repeat," *Biochemistry*, 49(47):10166-10178, 2010.

Gagnon et al., "Antisense and Antigen Inhibition of Gene Expression by Cell-Permeable Oligonucleotide-Oligospermine Conjugates," *Journal of the American Chemical Society* 133:8404-8407, 2011.

Grabczyk and Usdin, "Alleviating transcript insufficiency caused by Friedreich's ataxia triplet repeats," *Nucleic Acids Research*, 28(24):4930-4937, 2000.

Harper et al., "RNA interference improves motor and neuropathological abnormalities in a Huntington's disease mouse model," *Proc. Natl. Acad. USA*, 102:5820-5825, 2005.

Hashem et al., "Chemotherapeutic deletion of CTG repeats in lymphoblast cells from DM1 patients," *Nucleic Acids Research*, 32(21):6334-6346, 2004.

Hasholt et al., "Antisense downregulation of mutant huntingtin in a cell model," *J. Gene. Med.*, 5:528-538, 2003.

Hu and Corey, "Inhibiting gene expression with peptide nucleic acid (PNA)—peptide conjugates that target chromosomal DNA," *Biochemistry*, 46:7581-7589, 2007.

Hu et al., "Allele-selective inhibition of ataxin-3 (ATX3) expression by antisense oligomers and duplex RNAs," *Biol Chem.*, 392(4):315-325, 2011.

Hu et al., "Allele-selective inhibition of huntingtin expression by switching to an miRNA-like RNAi mechanism," *Chem Biol.*, 17(11):1183-1188, 2010.

Hu et al., "Allele-selective inhibition of mutant huntingtin by peptide nucleic acid-peptide conjugates, locked nucleic acid, and small interfering RNA," *Ann N Y Acad Sci.*, 1175:24-31, 2009.

Hu et al., "Allele-specific silencing of mutant huntingtin and ataxin-3 genes by targeting expanded CAG repeats in mRNAs," *Nat Biotechnol.*, 27(5):478-484, 2009.

Hu et al., "Cellular localization and allele-selective inhibition of mutant huntingtin protein by peptide nucleic acid oligomers containing the fluorescent nucleobase [bis-o-(aminoethoxy)phenyl]pyrrolocytosine," *Bioorg Med Chem Lett.*,19(21):6181-6184, 2009.

Lee et al., "Imaging gene expression in the brain in vivo in a transgenic mouse model of Huntington's disease with an antisense radiopharmaceutical and drug-targeting technology," *The Journal of Nuclear Medicine*, 43(7):948-956, 2002.

PCT International Preliminary Report on Patentability issued in International Application No. PCT/US2009/051938, mailed Feb. 10, 2011.

PCT International Search Report and Written Opinion issued in International Application No. PCT/US2009/051938, mailed Oct. 20, 2009.

Rodriguez-Lebron and Paulson, "Allele-specific RNA interference for neurological disease," *Gene Therapy*, 13:576-581, 2006.

Sah and Aronin, "Oligonucleotide therapeutic approaches for Huntington disease," *Journal of Clinical Investigation*, 121(2):500-507, 2011.

Schwarz et al., "Designing siRNA that distinguish between genes that differ by a single nucleotide," *PLOS Genetics*, 2:1307-1318, 2006.

Taneja, "Localization of trinucleotide repeat sequences in myotonic dystrophy cells using a single fluorochrome-labeled PNA probe," *BioTechniques*, 24(3):472-476, 1998.

Anderson et al., "An Overview of Psychiatric Symptoms in Huntington's Disease" Current Psychiatry Reports (2001) 3:379-388.

Boffa et al., "Isolation of active genes containing CAG repeats by DNA strands invasion by a peptide nucleic acid" PNAS (1995) 92:1901-5.

Borovecki et al., "Genome-wide expression profiling of human blood reveals biomarkers for Huntington's disease" *Proc. Natl. Acad. Sci. USA* (2005) 102:11023-11028.

Caplen et al., "Rescue of polyglutamine-mediated cytotoxicity by double-stranded RNA-mediated RNA interference" Human Molecular Genetics (2002) 11(2):175-184.

Chang et al., "Structural Analysis of Complementary DNA and Amino Acid Sequences of Human and Rat Androgen Receptors" PNAS (1988) 85:7211-7215.

Chin "On the Preparation and Utilization of Isolated and Purififed Oligonucleotides." Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Davidson et al., "Molecular medicine for the brain: silencing of disease genes with Rna interference" Lancet Neurol. (2004) 3:145-149.

Diaz-Hernandez et al., "Full Motor Recovery Despite Striatal Neuron Loss and Formation of Irreversible Amyloid-Like Inclusions in a Conditional Mouse Model of Huntington's Disease" *J. Neurosci* (2005) 25:9773-9781.

Eder et al., "Inhibition of LNCaP Prostate Cancer Cells by Means of Androgen Receptor Antisense Oligonucleotides" Cancer Gene Therapy (2000) 7(7):997-1007.

Gonzalez-Alegre et al., "Technology Insight: therapeutic RNA interference—how far from the neurology clinic?" Nature Clinical Practice 3:394-404, 2007.

Haque et al., "Antisense gene therapy for neurodegenerative disease" *Experimental Neurology* (1997) 144:139-146.

Harper et al., "Ten years of presymptomatic testing for Huntington's disease: the experience of the UK Huntington's Disease Prediction Consortium" J. Med. Genet. 37:567-571, 2000.

Hersch et al., "Translating Therapies for Huntington's Disease from Genetic Animal Models to Clinical Trials" *NeuroRX* (2004) 1:298-306.

Hersch et al., "Neuroprotection for Huntington's disease: Ready, set, slow" Neurotherapeutics (2008) 5(2):226-236.

Kordasiewicz et al., "Sustained Therapeutic Reversal of Huntington's Disease by Transient Repression of Huntingtin Synthesis" Neuron (2012) 74:1031-1044.

Liu et al., "Specific inhibition of Huntington's disease gene expression by siRNAs in cultures cells" *Proceedings of the Japan Academy. Series B, Physical and Biological Sciences* (2003) 79B:293-298.

MacDonald et al., "A novel gene containing a trinucleotide repeat that is expanded and unstable on Huntington's disease chromosomes" Cell (1993) 72(6):971-983.

Machida et al., "rAAV-mediated shRNA ameliorated neuropathology in Huntington disease model mouse" *Biochem. Biophys. Res. Commun.* (2006) 343:190-197.

MacMillan et al., "Molecular analysis and clinical correlations of the Huntington's disease mutation" Lancet (1993) 342:954-958.

Maher et al., "Comparative hybrid arrest by tandem antisense oligodeoxyribonucleotides or oligodeoxyribonucleoside methylphosphonates in a cell-free system" *Nuc. Acid. Res.* (1988) 16:3341-3358.

Martin et al., "38. Ein neuer Zugang zu 2'-O-Alkylribonucleosiden und Eigenschaften deren Oligonucleotide" *Helv. Chim. Acta* (1995) 78:486-504.

Nellemann et al., "Inhibition of Huntington synthesis by antisense oligonucleotides" *Molecular and Cellular Neurosciences* (2000) 16:313-323.

(56) References Cited

OTHER PUBLICATIONS

Nguyen et al., "Clioquinol down-regulates mutant huntingtin expression in vitro and mitigates pathology in a Huntington's disease mouse model" *PNAS* (2005) 102:11840-11845.

Nikiforov et al., "The Use of Phosphorothioate Primers and Exonuclease Hydrolysis for the Preparation of Single-stranded PCR Products and their Detection by Solid-phase Hybridization" PCR Methods and Applications (1994) 3:285-291.

Reynolds et al., "Rational siRNA design for RNA interference" Nature Biotechnology (2004) 22:326-330.

Sanghvi et al., "Heterocyclic Base Modifications in Nucleic Acids and Their Applications in Antisense Oligonucleotides" Antisense Research and Applications (1993) pp. 273-288.

Sheehan et al., "Biochemical properties of phosphonoacetate and thiophosphonoacetate oligodeoxyribonucleotides" *Nucleic Acids Research* (2003) 31:4109-4118.

Uhlmann et al., "Antisense oligonucleotides: a new therapeutic principle" *Chemical Reviews* (1990) 90:543-584.

Vickers et al., "Efficient Reduction of Target RNAs by Small Interfering RNA and Rnase H-dependent Antisense Agents. A comparative analysis." J Biol. Chem. (2003) 278:7108-7118.

Wang et al., "Clinico-pathological rescue of a model mouse of Huntington's disease by siRNA" *Neurosci. Res.* (2005) 53:241-249.

Woolf et al., "Specificity of antisense oligonucleotides in vivo" *Proc. Natl. Acad. Sci. USA* (1992) 89:7305-7309.

Yen et al., "Sequence-specific cleavage of Huntingtin mRNA by catalytic DNA" Annals of Neurology (1999) 46(3):366-373.

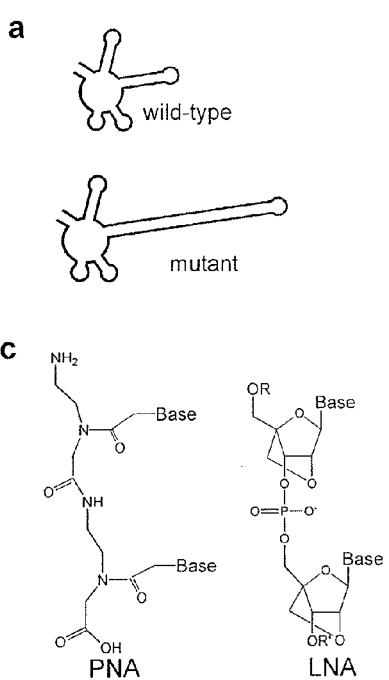
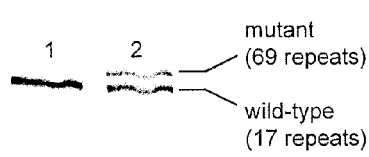
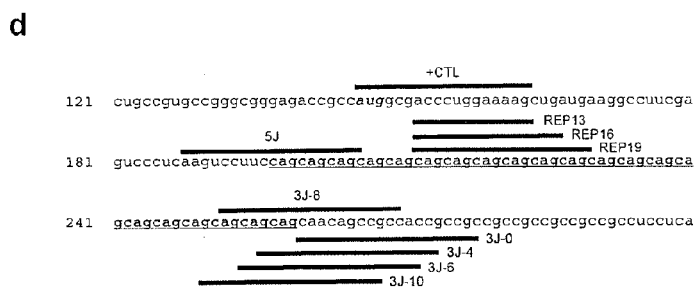
FIG. 1A-D

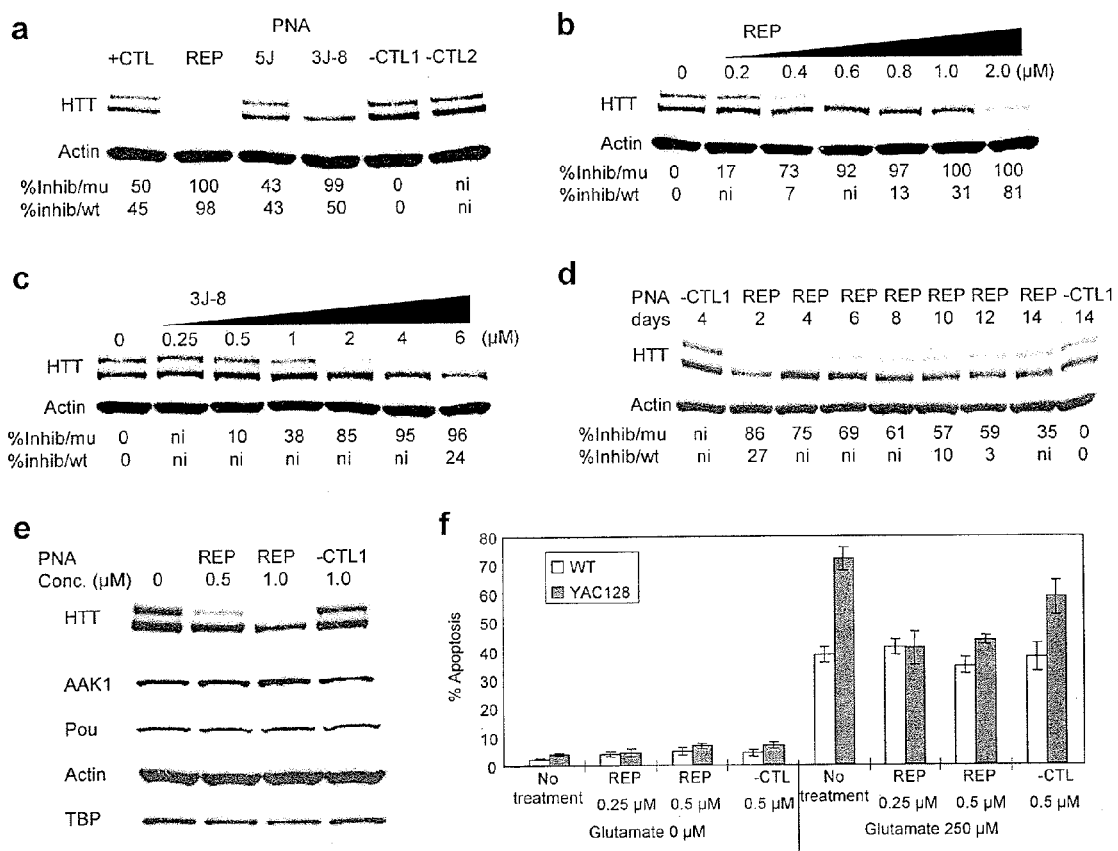
FIG. 2A-F

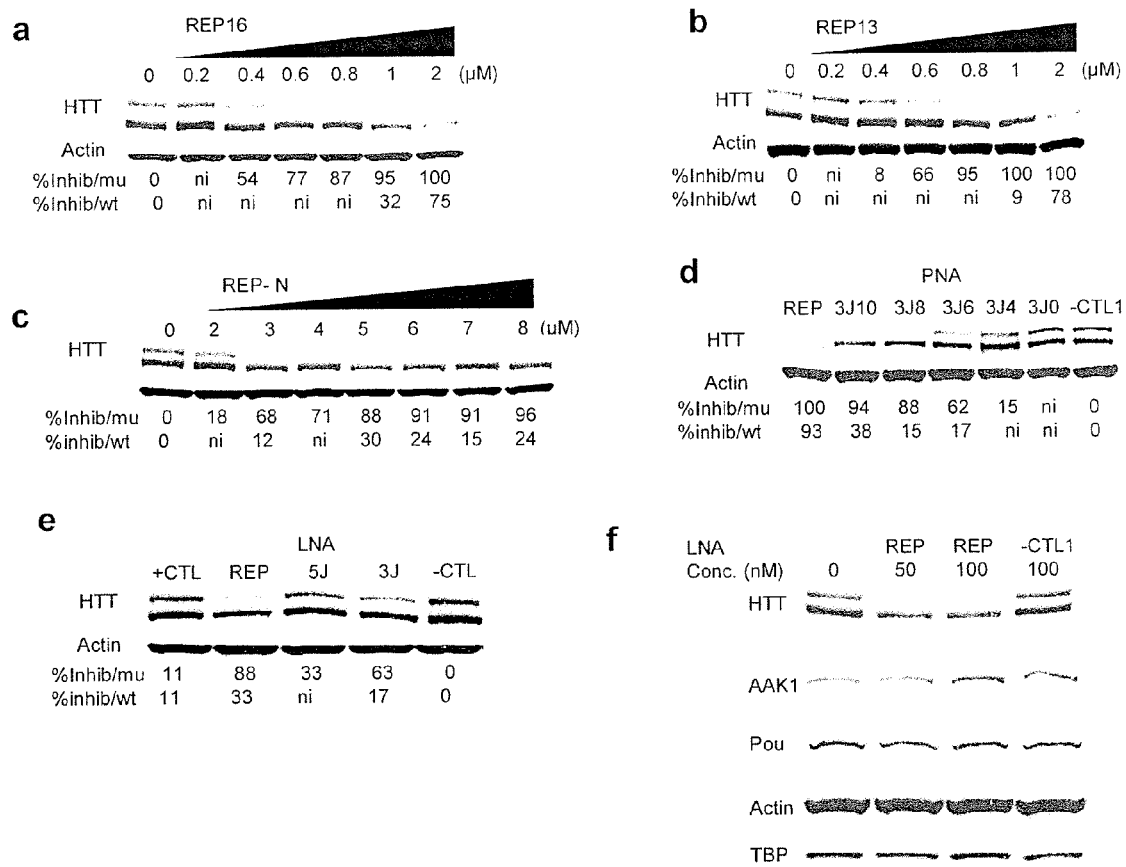
FIG. 3A-F

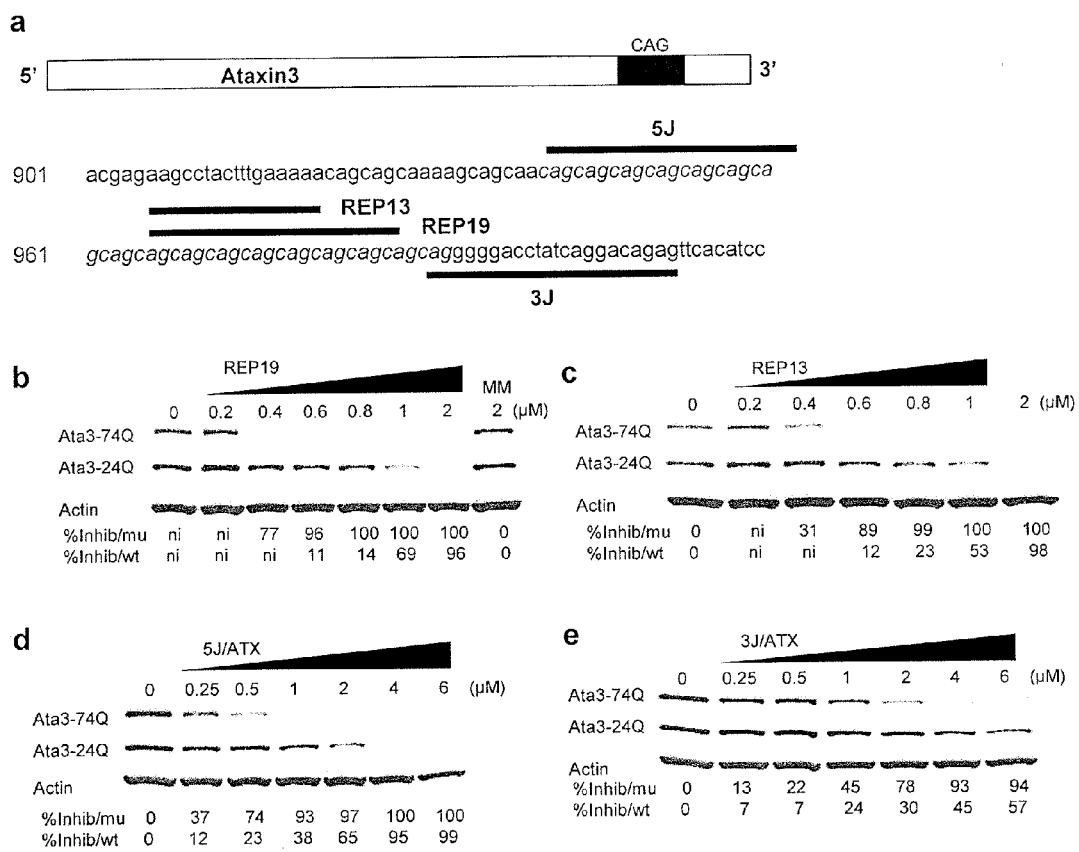
FIG. 4A-E

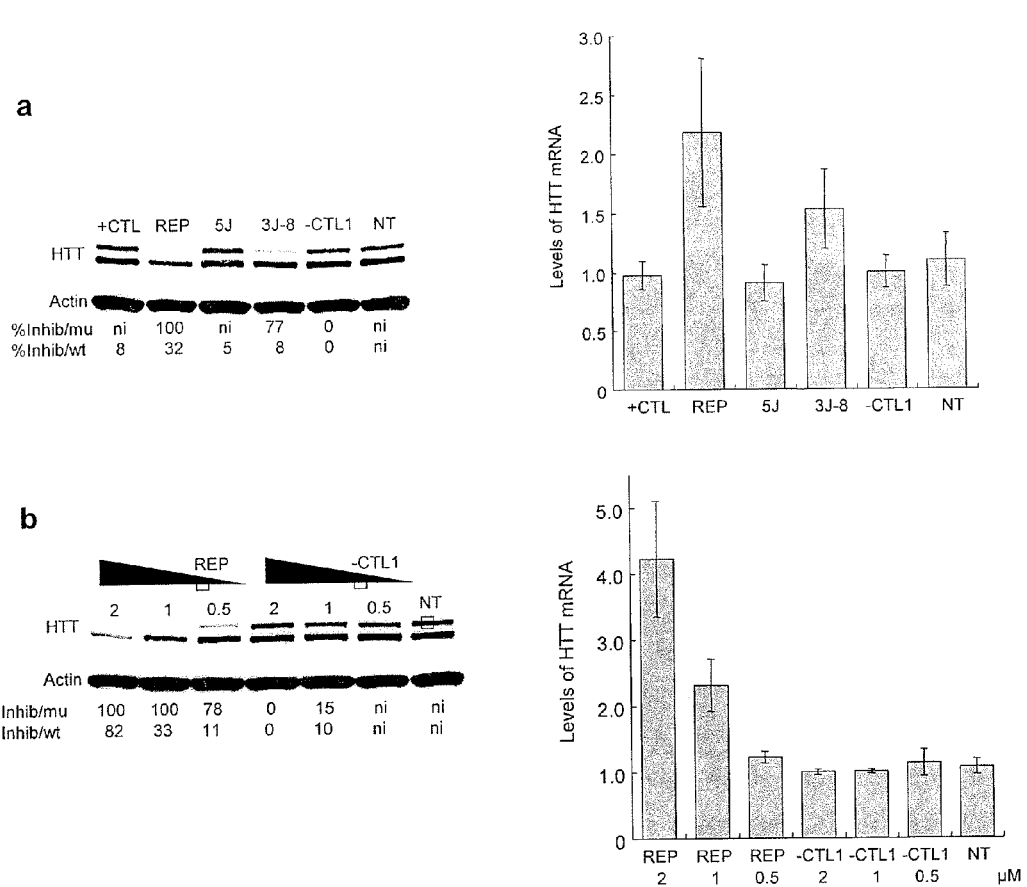
FIG. 5A-B

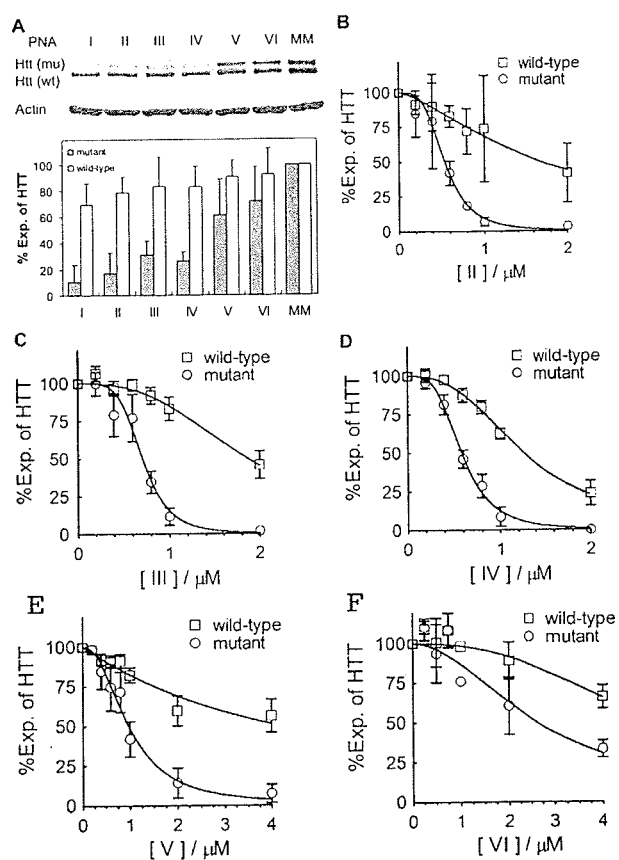
FIG. 11A-F

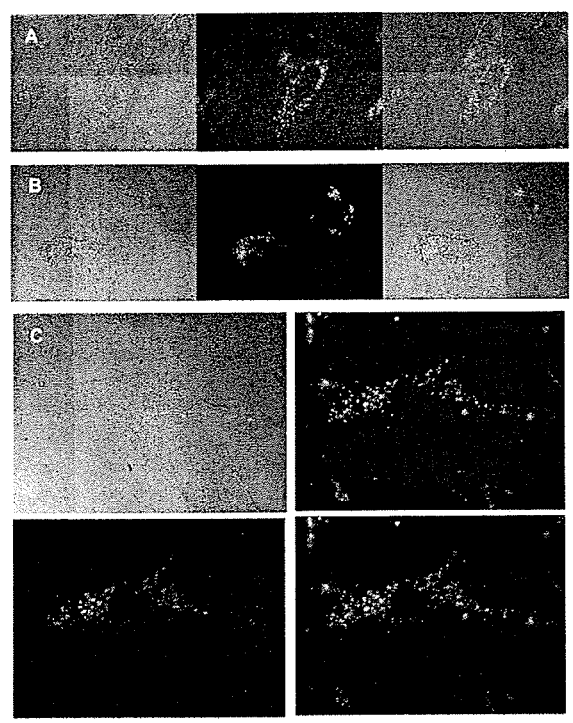
FIG. 12A-C

SELECTIVE INHIBITION OF POLYGLUTAMINE PROTEIN EXPRESSION

PRIORITY INFORMATION

The present application is a national phase application under 35 U.S.C. §371 of International Patent Application No. PCT/U.S.2009/051938 filed Jul. 28, 2009 which claims benefit of priority to U.S. Provisional Application No. 61/084, 350, filed Jul. 29, 2008 The entire text of each of the above-referenced disclosures are specifically incorporated herein by reference without disclaimer.

STATEMENT REGARDING FEDERALLY SPONSORED RESEARCH OR DEVELOPMENT

This invention was made in part with government support under Grant No. 60642 awarded by the National Institutes of Health-NIGMS. The United States Government has certain rights in the invention.

BACKGROUND OF THE INVENTION

A. Field of the Invention

The invention relates to the fields of biology and medicine. More particularly, the invention provides compositions and methods for the selective inhibition of triplet-encoded disease protein expression, such as Huntingtin and Ataxins 1-3.

B. Related Art

Huntington's Disease (HD) is an autosomal dominant inherited disorder with a incidence of 5-10 per 100,000 individuals in Europe and North America (Borrell-Pages et al., 2004; Walker, 2007). HD is caused by the expansion of CAG trinucleotide repeats within the first exon of the huntingtin (HTT) gene, leading to disruption of protein function, and neurodegeneration (Gusella and MacDonald, 2006). Antisense oligonucleotides or siRNAs that reduce HTT expression have been proposed as a therapeutic strategy (Hasholt et al., 2003; Boado et al., 2002; Harper et al., 2005; Denovan-Wright and Davidson, 2006; DiFiglia et al., 2007) but most oligomers inhibit the mutant and wild-type protein expression indiscriminately. HTT is known to play an essential role in embryogenesis (Nasir et al., 1995), neurogenesis (White et al., 1997), and normal adult function in heterozygotes (Nasir et al., 1995), suggesting that agents inhibiting both mutant and wild-type HTT will induce significant side-effects. One strategy for distinguishing mutant from wild-type alleles for HD and other neurological diseases uses siRNAs that target single nucleotide differences (Schwarz et al., 2006; Rodriguez-Lebron and Paulson, 2006). These polymorphisms will often differ from patient to patient, complicating application of allele-specific RNAi in the clinic. Thus, there remains a need to identify agents that selectively inhibit mutant HTT production.

SUMMARY OF THE INVENTION

Thus, in accordance with the present invention, there is provided a method for inhibiting expression of a disease protein encoded by an mRNA having expanded tri-nucleotide repeat region comprising contacting a cell that produces said disease protein with an amount of a nucleic acid analog that targets said repeat region in said mRNA, wherein (i) inhibiting is selective for said disease protein over a normal form of said disease protein, an mRNA for which lacks an expanded tri-nucleotide repeat region, and (ii) inhibiting does not substantially affect production of said mRNA. The repeat region may be about 151 repeats or 125 repeats or less in size. The disease protein may be Huntingtin, ataxin-3, ataxin-1, ataxin-2 or atrophin1.

The nucleic acid analog may be about 7 to about 30 bases in length. The nucleic acid analog may be a peptide-nucleic acid (PNA) or a locked nucleic acid (LNA), may further comprise a cationic peptide, and/or may further target the junction of a tri-nucleotide repeat region. The nucleic acid analog may lack bases that recruit RNAseH. The nucleic acid analog may be formulated in a lipid vehicle. The PNA may comprise at least one modified base, such as [bis-o-(amino ethoxy)phenyl]pyrrolocytosine.

In another embodiment, there is provided a method for inhibiting expression, in a subject, of a disease protein encoded by an mRNA having expanded tri-nucleotide repeat region comprising administering to said subject an amount of a nucleic acid analog that targets said repeat region in said mRNA, wherein (i) inhibiting is selective for said disease protein over a normal form of said disease protein, an mRNA for which lacks an expanded tri-nucleotide repeat region, and (ii) inhibiting does not substantially affect production of said mRNA. The repeat region may be about 151 repeats or 125 repeats or less in size. The disease protein may be Huntingtin, ataxin-3, ataxin-1, ataxin-2 or atrophin1.

The nucleic acid analog may be about 7 to about 30 bases in length. The nucleic acid analog may be a peptide-nucleic acid (PNA) or a locked nucleic acid (LNA), may further comprise a cationic peptide, and/or may further target the junction of a tri-nucleotide repeat region. The PNA may comprise at least one modified base, such as [bis-o-(aminoethoxy)phenyl]pyrrolocytosine. The nucleic acid analog may lack bases that recruit RNAseH. The nucleic acid analog may administered more than one, such as at least about once every week. The nucleic acid analog may be administered orally, intravenously, intraarterially, intramuscularly or into the CNS. The nucleic acid analog may be administered in a lipid formulation. The method may further comprising administering a second therapy to said subject.

In yet another embodiment, there is provided a composition of matter comprising a nucleic acid analog that targets an mRNA encoding an expanded tri-nucleotide repeat region for a disease protein. The nucleic acid analog may target said repeat region, and may further target a repeat region junction. The nucleic acid analog may be about 7 to about 30 bases in length. The nucleic acid analog may be a peptide-nucleic acid (PNA) or a locked nucleic acid (LNA), and may further comprise a cationic peptide. The PNA may comprise at least one modified base, such as [bis-o-(aminoethoxy)phenyl]pyrrolocytosine. The nucleic acid analog may lack bases that recruit RNAseH. The nucleic acid analog may be dispersed in a lipid vehicle.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to these drawings and the detailed description presented below.

FIGS. 1A-D. Triplet repeats as targets for synthetic oligomers. (FIG. 1A) Schematic of the CONTRAfold prediction of the HTT CAG triplet repeat and adjacent RNA regions. Predicted hairpin structure is larger for the expanded mutant repeats than for the wild-type repeat region (CAG repeat region shown in red). Because of space constraints, the length of the hairpin containing the mutant CAG sequence is not drawn to scale. The differences between mutant and wild-type repeats in GM04281 cells would be larger. (FIG. 1B) Western analysis showing that wild-type and mutant HTT protein can be separated by gel electrophoresis. The left lane shows HTT from GM04795, a fibroblast cell line that is homozygous for wild-type HTT. The right lane shows HTT from GM04281, a fibroblast cell line that is heterozygous for mutant HTT. (FIG. 1C) Chemical structures of PNA and LNA. (FIG. 1D) Target sites for oligomers within HTT mRNA (NM_002111). The HTT gene is shown from +121 to 300 (SEQ ID NO:29). The AUG translation start is italicized, the CAG repeat region is in bold-face (to save space the inventors show only 21 repeats, more repeats would be present in repeat regions from HD patients).

FIGS. 2A-F. Inhibition to HTT expression by PNA-peptide conjugates. All data show western analysis of protein levels. Unless otherwise noted experiments use GM04281 fibroblast cells that are heterozygous for mutant HTT expression. (FIG. 2A) Effect on HTT expression of adding 5 μM PNA-peptide conjugates to GM04281 cells. (FIG. 2B) Effect on HTT expression of adding increasing concentrations of PNA conjugate REP. (FIG. 2C) Effect on HTT expression of adding increasing concentrations of PNA conjugate 3J-8. (FIG. 2D) Timecourse of inhibition of HTT expression by PNA conjugate REP (1 μM) for 2-14 days after transfection. (FIG. 2E) Effect of adding REP on expression of other proteins with mRNAs that contain CAG repeats. (FIG. 2F) Glutamate-induced apoptosis of WT and YAC128 mouse striatal neurons (MSN) treated with or without PNA conjugates. PNA conjugate REP were added at the concentration of 0.25 μM and 0.5 μM, 4 days before the glutamate application. Non-complementary PNA conjugate −CTL1 was added at 0.5 μM. MSN were exposed to 250 μM glutamate for 7 h, fixed, permeabilized and analyzed by TUNEL staining and PI counterstaining The fraction of TUNEL-positive is shown for WT (open bars) and YAC128 (filled bars) MSN. The data are presented as mean±SE (n=6-8 microscopic fields, 100-300 MSN per field). Apoptosis of YAC128 MSN is significantly (p<0.05) reduced by the addition of REP when treated with 250 μM glutamate. Data representative of duplicate experiments.

FIGS. 3A-F. Inhibition of HTT expression by modified PNA designs and LNAs. All data show western analysis of protein levels in GM04281 fibroblast cells. Effect on HTT expression of adding increasing concentrations of REP16 (FIG. 3A) or REP13 (FIG. 3B). (FIG. 3C) Effect on HTT expression of adding increasing concentrations of REP-N-$K_8$. (FIG. 3D) Effect on HTT expression of 2 μM PNA conjugates 3J-0, 3J-4, 3J-6, 3J-8, and 3J-10 that target related sequences at the 3' junction. (FIG. 3E) Effect on HTT expression of adding 100 nM concentrations of LNAs. (FIG. 3F) Effect of adding LNA/REP on expression of other proteins with mRNAs that contain CAG repeats.

FIGS. 4A-E. Potent and selective inhibition of mutant ataxin-3. All data show western analysis of ataxin-3 expression in GM06151 fibroblast cells. (FIG. 4A) Target sites for oligomers within the ataxin-3 gene (SEQ ID NO:30). (FIG. 4B) Inhibition of ataxin-3 expression by PNA conjugate REP19. (FIG. 4C) Inhibition of ataxin-3 expression by PNA conjugate REP13. (FIG. 4D) Inhibition of ataxin-3 expression by PNA conjugate 5J/ATX. (FIG. 4E) Inhibition of ataxin-3 expression by PNA conjugate 3JATX.

FIGS. 5A-B. Anti-HTT PNAs do not reduce HTT mRNA levels. (FIG. 5A) Effect on adding PNA-peptide conjugates on expression of HTT protein (western analysis, left) and HTT mRNA (quantitative PCR, right) in GM04281 fibroblast cells. All conjugates were added at a concentration of 1 μM (FIG. 5B) Effect of adding PNA-peptide conjugate REP or −CTL1 at 0.5, 1 and 2 μM on levels of HTT protein (western analysis, left) or mRNA (quantitative PCR, right). NT=no treatment (no conjugate added).

(FIG. 7A) Effect on HTT expression of adding 100 nM concentrations of duplex siRNAs. (FIG. 7B) Effect on HTT expression of adding increasing concentrations of siRNA/REP. (FIG. 7C) Effect on HTT expression of adding increasing concentrations of siRNA/5J. (FIG. 7D) Effect on HTT expression of adding increasing concentrations of siRNA/3J. Duplex RNAs were introduced using cationic lipid.

FIGS. 11A-F. Modified PNAs selectively inhibit mutant HTT expression in fibroblasts GM04281. (FIG. 11A) Top, western analysis the effects of PNAs I-VI on HTT expression. Bottom, quantitation of inhibition of mutant and wild-type HTT by PNAs I-VI. PNAs were added at 1 μM concentration. (FIGS. 11B-F) Effects of PNAs II-VI on HTT expression at varied concentrations. Experiments were performed in triplicate. Expression is relative to expression to untreated cells.

FIGS. 12A-C. Fluorescent microscopy of PNA II in living fibroblasts. PNA was added at 1 μM concentration. (FIG.

12A) One day or (FIG. 12B) nine days after PNA transfection. Left, Differential interference contrast microscopy (DIC) image; middle, PNA fluorescent; right, overlay of DIC and fluorescent images. (FIG. 12C) PNA was co-localized with endosome marker Transferrin. 1 µM of Htt2 was co-incubate with 25 µg/mL of Transferrin-Alexa Fluor 633 for 15 h in fibroblast cells. Upper left, DIC image; upper right, PNA alone; lower left, transferrin fluorescent; lower right, overlay of PNA and transferrin images.

DETAILED DESCRIPTION OF THE INVENTION

Figure 6:
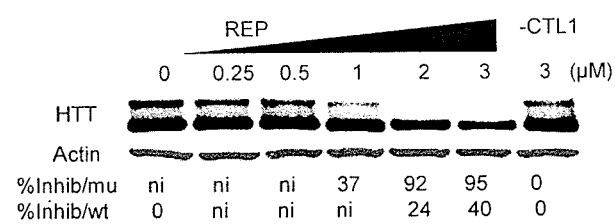
FIG. 6. Inhibition of neuronal/cell glial cell mixture by PNA REP. HTT protein levels were analyzed by western analysis. PNAs REP or −CTL1 were added at the indicated concentrations. Medium striatal spiny neurons (MSN) and supporting glial cells were harvested from mice and cultured as described in Materials and Methods. Levels of inhibition reflect HTT levels in both glial and MSN cells. Because glial cells make up a large majority (~90%) of the cells in culture, data should not be taken as a direct indication of the level of inhibition of HTT in MSN cells. Cells were treated with PNA and harvested in parallel with cells used form neuroprotection assays (FIG. 2F). The top HTT band is human HTT, the bottom is murine HTT.
Figure 7:
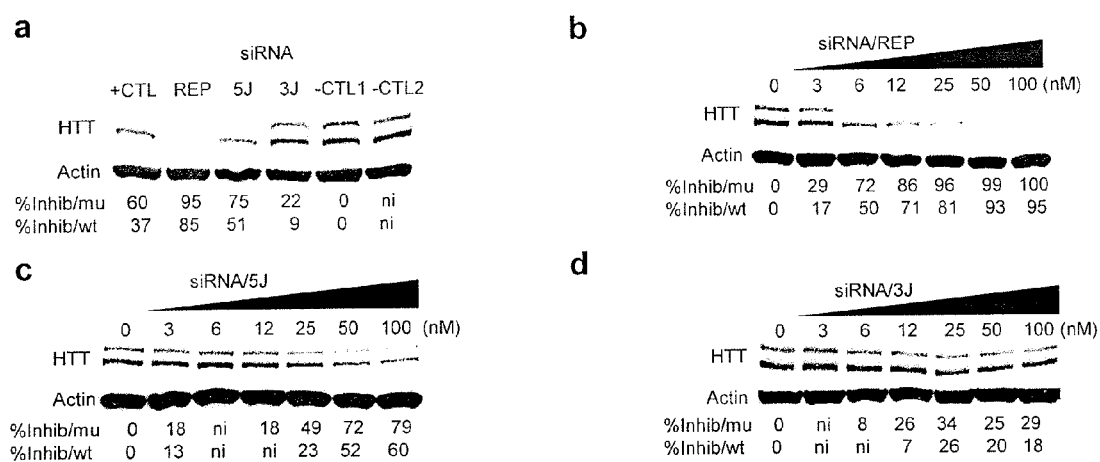
FIGS. 7A-D. Inhibition of HTT expression by duplex RNAs. All data show western analysis of protein levels in GM04281 fibroblast cells.

As discussed above, CAG-repeat related diseases present significant obstacles with respect to the selective inhibition of disease versus normal protein production. As shown in the data here presented by the inventors, single-stranded nucleic acid analogs (NAAs) can exploit differences in the number of triplet repeats and can achieve allele-selective inhibition of expression of HTT or ataxin-3. Selectivity is achieved even though complementary target sequences also exist within both mutant and wild-type mRNAs. For HTT, the target can be within the CAG repeat or at the 3' junction between the repeat and the rest of the HTT gene. For ataxin-3, the repeat, the 3' junction, and the 5' junction are all productive targets Inhibition is robust and can be achieved by a wide range of different PNAs and LNAs. The broad base of inhibitory compounds permits design of improved agents with enhanced potencies and selectivities.

Two observations are worth making. The first is that single-stranded NAAs can discriminate among identical sequences inside cells on the basis of context—in this case length of the repeat and the potential to form energetically different structures—rather than sequence. The second is that the potential for developing single-stranded analogs as treatment for genetic disease appears greater than had been appreciated. Exploiting the surprising ability of NAAs to selectively recognize mutant repeat nucleic acid sequences offers a promising strategy for developing therapies for Huntington's Disease, Machado-Joseph Disease, spinocerebellar ataxias and other triplet repeat disorders.

I. POLYGLUTAMINE REPEAT DISEASES

The polyglutamine disorders include nine neurodegenerative disorders that are inherited gain-of-function diseases caused by expansion of a translated CAG repeat. Even though the disease-causing proteins are widely expressed, specific collections of neurons are more susceptible in each disease. There is substantial evidence linking the function of the polyglutamine disease-associated proteins with the regulation of gene transcription, and a variety of mechanisms have been suggested by which the polyglutamine proteins impact upon transcription, including altering the function of a very specific DNA-binding factor like the AR (SBMA), general DNA-binding proteins like TBP (SCA17), Sp1, TFIID and TFIIF (HD), chromatin structure (SCA7), coregulators (HD, SCA1, and DRPLA), and possibly the ubiquitin-proteasome system (SCA3). There also is evidence they impact other biological processes important for neuronal function, for example, intracellular trafficking (Gunawardena and Goldstein, 2005) and the mitochondrial/energy metabolism (Browne and Beal, 2004). Some of these disorders are discussed in greater detail below.

A. Huntington Disease

Huntington disease, also called Huntington's chorea, chorea major, or HD, is a genetic neurological disorder characterized by abnormal body movements called chorea and a lack of coordination; it also affects a number of mental abilities and some aspects of behavior. In 1993, the gene causing HD was found, making it one of the first inherited genetic disorders for which an accurate test could be performed. The accession number for Huntingtin is NM_002111.

The gene causing the disorder is dominant and may, therefore, be inherited from a single parent. Global incidence varies, from 3 to 7 per 100,000 people of Western European descent, down to 1 per 1,000,000 of Asian and African descent. The onset of physical symptoms in HD occur in a large range around a mean of a person's late forties to early fifties. If symptoms become noticeable before a person is the age of twenty, then their condition is known as Juvenile HD.

A trinucleotide repeat expansion occurs in the Huntingtin gene, which produces mutant Huntingtin protein. The presence of this protein increases the rate of neuron cell death in select areas of the brain, affecting certain neurological functions. The loss of neurons isn't fatal, but complications caused by symptoms reduce life expectancy. There is currently no proven cure, so symptoms are managed with a range of medications and supportive services.

Symptoms increase in severity progressively, but are not often recognised until they reach certain stages. Physical symptoms are usually the first to cause problems and be noticed, but these are accompanied by cognitive and psychiatric ones which aren't often recognized. Almost everyone with HD eventually exhibits all physical symptoms, but cognitive symptoms vary, and so any psychopathological problems caused by these, also vary per individual. The symptoms of juvenile HD differ in that they generally progress faster and are more likely to exhibit rigidity and bradykinesia instead of chorea and often include seizures.

The most characteristic symptoms are jerky, random, and uncontrollable movements called chorea, although sometimes very slow movement and stiffness (bradykinesia, dystonia) can occur instead or in later stages. These abnormal movements are initially exhibited as general lack of coordination, an unsteady gait and slurring of speech. As the disease progresses, any function that requires muscle control is affected, this causes reduced physical stability, abnormal facial expression, impaired speech comprehensibility, and difficulties chewing and swallowing. Eating difficulties commonly cause weight loss. HD has been associated with sleep cycle disturbances, including insomnia and rapid eye movement sleep alterations.

Selective cognitive abilities are progressively impaired, including executive function (planning, cognitive flexibility, abstract thinking, rule acquisition, initiating appropriate actions and inhibiting inappropriate actions), psychomotor function (slowing of thought processes to control muscles), perceptual and spatial skills of self and surrounding environment, selection of correct methods of remembering information (but not actual memory itself), short-term memory, and ability to learn new skills, depending on the pathology of the individual.

Psychopathological symptoms vary more than cognitive and physical ones, and may include anxiety, depression, a reduced display of emotions (blunted affect) and decreased ability to recognize negative expressions like anger, disgust, fear or sadness in others, egocentrism, aggression, and compulsive behavior. The latter can cause, or worsen, hypersexuality and addictions such as alcoholism and gambling.

HD is autosomal dominant, needing only one affected allele from either parent to inherit the disease. Although this generally means there is a one in two chance of inheriting the disorder from an affected parent, the inheritance of HD is more complex due to potential dynamic mutations, where DNA replication does not produce an exact copy of itself. This can cause the number of repeats to change in successive generations. This can mean that a parent with a count close to the threshold, may pass on a gene with a count either side of the threshold. Repeat counts maternally inherited are usually similar, whereas paternally inherited ones tend to increase. This potential increase in repeats in successive generations is known as anticipation. In families where neither parent has HD, new mutations account for truly sporadic cases of the disease. The frequency of these de novo mutations is extremely low.

Homozygous individuals, who carry two mutated genes because both parents passed on one, are rare. While HD seemed to be the first disease for which homozygotes did not differ in clinical expression or course from typical heterozygotes, more recent analysis suggest that homozygosity affects the phenotype and the rate of disease progression though it does not alter the age of onset suggesting that the mechanisms underlying the onset and the progression are different.

Huntingtin protein is variable in its structure as there are many polymorphisms of the gene which can lead to variable numbers of glutamine residues present in the protein. In its wild-type (normal) form, it contains 6-35 glutamine residues; however, in individuals affected by HD, it contains between 36-155 glutamine residues. Huntingtin has a predicted mass of ~350 kDa, however, this varies and is largely dependent on the number of glutamine residues in the protein. Normal huntingtin is generally accepted to be 3144 amino acids in size.

Two transcriptional pathways are more extensively implicated in HD—the CBP/p300 and Sp1 pathways—and these are transcription factors whose functions are vital for the expression of many genes. The postulated relationship between CBP and HD stems from studies showing that CBP is found in polyglutamine aggregates (see Kazantsev et al., 1999). Consequently, it was demonstrated that huntingtin and CBP interact via their polyglutamine stretches, that huntingtin with an expanded polyglutamine tract interferes with CBP-activated gene expression, and that overexpression of CBP rescued polyglutamine-induced toxicity in cultured cells (Nucifora et al., 2001; Steffan et al., 2001). Mutant huntingtin was also shown to interact with the acetyltransferase domain of CBP and inhibit the acetyltransferase activity of CBP, p300, and the p300/CBP-associated factor P/CAF (Steffan et al., 2001).

These observations prompted a hypothesis whereby the pathogenic process was linked to the state of histone acetylation; specifically, mutant huntingtin induced a state of decreased histone acetylation and thus altered gene expression. Support for this hypothesis was obtained in a *Drosophila* HD model expressing an N-terminal fragment of huntingtin with an expanded polyglutamine tract in the eye. Administration of inhibitors of histone deacetylase arrested the neurodegeneration and lethality (Steffan et al., 2001). Protective effects of HDAC inhibitors have been reported for other polyglutamine disorders, prompting the concept that at least some of the observed effects in polyglutamine disorders are due to alterations in histone acetylation (Hughes 2002). Studies published in 2002 revealed that the N-terminal fragment of huntingtin and intact huntingtin interact with Sp1 (Dunah et al., 2002; Li et al., 2002), a transcriptional activator that binds to upstream GC-rich elements in certain promoters. It is the glutamine-rich transactivation domain of Sp1 that selectively binds and directs core components of the general transcriptional complex such as TFIID, TBP and other TBP-associated factors to Sp1-dependent sites of transcription. In vitro transcription studies have gone on to show that in addition to targeting Sp1, mutant huntingtin targets TFIID and TFIIF, members of the core transcriptional complex (Zhai et al. 2005). Mutant huntingtin was shown to interact with the RAP30 subunit of TFIIF. Notably, overexpression of RAP30 alleviated both mutant huntingtin-induced toxicity and transcriptional repression of the dopamine D2 receptor gene. These results indicate that mutant huntingtin may interfere with multiple components of the transcription machinery.

There is no treatment to fully arrest the progression of the disease, but symptoms can be reduced or alleviated through the use of medication and care methods. Huntington mice models exposed to better husbandry techniques, especially better access to food and water, lived much longer than mice that were not well cared for.

Standard treatments to alleviate emotional symptoms include the use of antidepressants and sedatives, with antipsychotics (in low doses) for psychotic symptoms. Speech therapy helps by improving speech and swallowing methods; this therapy is more effective if started early on, as the ability to learn is reduced as the disease progresses. A two-year pilot study, of intensive speech, pyschiatric and physical therapy, applied to inpatient rehabilitation, showed motor decline was greatly reduced.

Nutrition is an important part of treatment; most third and fourth stage HD sufferers need two to three times the calories of the average person to maintain body weight. Healthier foods in pre-symptomatic and earlier stages may slow down the onset and progression of the disease. High calorie intake in pre-symptomatic and earlier stages has been shown to speed up the onset and reduce IQ level. Thickening agent can be added to drinks as swallowing becomes more difficult, as thicker fluids are easier and safer to swallow. The option of using a stomach PEG is available when eating becomes too hazardous or uncomfortable; this greatly reduces the chances of aspiration of food, and the subsequent increased risk of pneumonia, and increases the amount of nutrients and calories that can be ingested.

EPA, an Omega-3 fatty acid, may slow and possibly reverse the progression of the disease. As of April 2008, it is in FDA clinical trial as ethyl-EPA, (brand name Miraxion), for prescription use. Clinical trials utilise 2 grams per day of EPA. In the United States, it is available over the counter in lower concentrations in Omega-3 and fish oil supplements.

B. Spinocerebellar Ataxias

Spinocerebellar ataxia (SCA) is one of a group of genetic disorders characterized by slowly progressive incoordination of gait and often associated with poor coordination of hands, speech, and eye movements. Frequently, atrophy of the cerebellum occurs. As with other forms of ataxia, SCA results in unsteady and clumsy motion of the body due to a failure of the fine coordination of muscle movements, along with other symptoms. The symptoms of the condition vary with the specific type (there are several), and with the individual patient. Generally, a person with ataxia retains full mental capacity but may progressively lose physical control.

There is no known cure for spinocerebellar ataxia, which is a progressive disease (it gets worse with time), although not all types cause equally severe disability. Treatments are generally limited to softening symptoms, not the disease itself. The condition can be irreversible. A person with this disease will usually end up needing to use a wheelchair, and eventually they may need assistance to perform daily tasks. The treatment of incoordination or ataxia, then mostly involves the use of adaptive devices to allow the ataxia individual to maintain as much independence as possible. Such devices may include a cane, crutches, walker, or wheelchair for those with impaired gait; devices to assist with writing, feeding, and self care if hand and arm coordination are impaired; and communication devices for those with impaired speech.

Many patients with hereditary or idiopathic forms of ataxia have other symptoms in addition to ataxia. Medications or other therapies might be appropriate for some of these symptoms, which could include tremor, stiffness, depression, spasticity, and sleep disorders, among others. Both onset of initial symptoms and duration of disease can be subject to variation, and it can be easily misdiagnosed as another neurological condition, such as multiple sclerosis (MS).

Spinocerebellar ataxia type 1 (SCA1) is an autosomal dominant ataxia that results in gait ataxia, dysarthria, and bulbar dysfunction, with death usually between 10 and 15 years after the onset of symptoms. The average age of onset is in the 4$^{th}$ decade of life. Despite the protein ataxin-1 being widely expressed in the central nervous system, the most frequently seen and most severe pathological alterations are restricted to loss of Purkinje cells in the cerebellar cortex, as well as loss of neurons in the inferior olivary nuclei, the cerebellar dentate nuclei and the red nuclei.

Normally ataxin-1, the product of the SCA1 gene, is prominently located in the nuclei of neurons (Servadio et al., 1995). Indication that SCA1 pathogenesis was due to alterations in nuclear function began with the observation that for mutant ataxin-1 to cause disease, it had to enter the nucleus of Purkinje cells (Klement et al., 1998). Consequent studies revealed that wild-type ataxin-1 has properties consistent with a role in the regulation of gene expression in the nucleus. These include the ability to bind RNA (Yue et al., 2001) and to shuttle between the nucleus and cytoplasm (Irwin et al., 2005).

Spinocerebellar ataxia type 2 (SCA2) is characterized by progressive cerebellar ataxia, including nystagmus, slow saccadic eye movements and, in some individuals, ophthalmoparesis. Pyramidal findings are present; deep tendon reflexes are brisk early on and are absent later in the course. Age of onset is typically in the 3$^{rd}$ to 4$^{th}$ decade with a 10-15-year disease duration.

The diagnosis of SCA2 rests upon the use of molecular genetic testing to detect an abnormal CAG trinucleotide repeat expansion of the ATXN2 gene. Affected individuals have alleles with greater than 32 CAG trinucleotide repeats. Such testing detects nearly 100% of cases and is available in clinical laboratories.

Management of individuals with SCA2 is supportive. Affected individuals should maintain activity. Canes and walkers help prevent falls; grab bars, raised toilet seats, and ramps to accommodate motorized chairs may be necessary. Speech therapy and communication devices such as writing pads and computer-based devices may benefit those with dysarthria. Weighted eating utensils and dressing hooks help maintain a sense of independence. When dysphagia becomes troublesome, video esophagrams can identify the consistency of food least likely to trigger aspiration. Vitamin supplements are recommended; weight control prevents difficulties with ambulation and mobility. Affected individuals should avoid alcohol and medications known to affect cerebellar function.

Spinocerebellar ataxia type 3 (SCA3), also known as Machado Joseph disease (MJD), is the most common of the autosomal dominantly inherited ataxias with several genetic features that distinguish it from many of the other polyglutamine disorders. In contrast to HD and SCAT, where the repeat threshold for mutant alleles is <40, in SCA3 the repeat threshold for the mutant alleles is >50 repeats. Moreover, although other polyglutamine disorders behave as pure dominant diseases, SCA3/MJD homozygous patients have a more severe disease presentation than individuals having only a single mutant allele. Onset is normally in the 4$^{th}$ decade, and duration averages about 10 years.

Ataxin-3 contains an N-terminal Josephin domain (JD) with recently ascribed ubiquitin protease activity (Burnett et al., 2003; Scheel et al., 2003), two ubiquitin interacting motifs (UIMs) capable of binding ubiquitin (Chai et al., 2004; Burnett et al., 2003; Donaldson et al., 2003) followed by a polyglutamine stretch, and a C-terminal variable domain. The crystal structure of the ataxin-3 JD provided insight into the potential function of ataxin-3 as a polyubiquitin chain editing protein by demonstrating a tight connection between polyubiquitin binding and the deubiquitylating activity of ataxin-3 (Mao et al., 2005; Nicastro et al., 2005). Thus, there are considerable structural data indicating that ataxin-3 has a role in the ubiquitin and/or the ubiquitin-proteasome system. Ataxin-3 is unique from the other polyglutamine diseases in that wild-type ataxin-3 expression in *Drosophila* protects neurons from toxicity initiated by other polyglutamine-expanded proteins (Warrick et al., 2005). This protection afforded by wild-type ataxin-3 was dependent on active proteasomes and both the UIM and ubiquitin protease domains of ataxin-3.

The accession numbers for these genes are as follows: Ataxin1 (NM_000332), ataxin2 (NM_002973), and ataxin3 (NM_004993).

C. Dentatorubral and Pallidoluysian Atrophy (DRPLA)

Dentatorubral-pallidoluysian atrophy (DRPLA) is an autosomal dominant spinocerebellar degeneration caused by an expansion of a CAG repeat encoding a polyglutamine tract in the atrophin-1 protein. It is also known as Haw River Syndrome and Naito-Oyanagi disease. Several sporadic cases have been reported from Western countries, but this disorder seems to be very rare except in Japan.

DRPLA can be juvenile-onset (<20 years), early adult-onset (20-40 years), or late adult-onset (>40 years). Late adult-onset DRPLA is characterized by ataxia, choreoathetosis and dementia. Early adult-onset DRPLA also includes seizures and myoclonus. Juvenile-onset DRPLA presents with ataxia and symptoms consistent with progressive myoclonus epilepsy.

Atrophin-1 (ATN1) encodes a hydrophilic 1184 amino acid protein with several repetitive motifs including a serine-rich region, a variable length polyglutamine tract, a polyproline tract, and a region of alternating acidic and basic residues. It contains a putative nuclear localization signal in the N-terminus of the protein and a putative nuclear export signal in the C-terminus. ATN1 is ubiquitously expressed in all tissues, but proteolytically cleaved in neuronal cells. The function of ATN1 is not clear, however it is believed to be a transcriptional co-repressor. ATN1 and atrophin-2 can be co-immunoprecipitated, indicating that they may carry out some functions together in a molecular complex. Atrophin-1 may be a dispensable or redundant protein as mice bred with a null allele for atrophin-1 produce viable and fertile offspring and show no compensatory upregulation of atrophin-2. The accession number for atrophin1 is NM_001940.

DRPLA is characterized by marked, generalized brain atrophy and the accumulation of atrophin-1 with expanded glutamine stretches. Mutant atrophin-1 proteins have been found in neuronal intranuclear inclusions (NII) and diffusely accumulated in the neuronal nuclei. While the role of NIIs (pathologic or protective) is unclear, the diffuse accumulation of mutant protein is regarded as toxic.

There is significant reduction in CNS tissue throughout the brain and spinal cord, with brain weights of DRPLA patients often becoming less than 1000 g. In regions lacking obvious neuronal depletion, atrophy of the neuropil is noted. The globus pallidus (lateral greater than medial segment) and subthalamic nucleus demonstrate consistent neuronal loss and astrocytic gliosis. The dentate nucleus shows neuronal loss with the remaining atrophic neurons exhibiting grumose degeneration. In general, the pallidoluysian degeneration is more severe than the dentatorubral degeneration in juvenile-onset and the reverse is true for the late adult-onset.

Transgenic DRPLA mice demonstrated several neuronal abnormalities including a reduction in the number and size of dendritic spines as well as in the area of perikarya and diameter of dendrites. Spine morphology and density have been linked to learning and memory functions as well as epilepsy. The stubby-type spines seen in DRPLA mice are morphologically different from the thin and mushroom-type spines seen in Huntington's mice.

Morphometric analysis of DRPLA mouse brains has shown a loss of normal inter-microtubule spacing in neuronal axons. The microtubules were relatively compacted, suggesting abnormalities in protein transport may play a role in neuronal degeneration. In humans, atrophin-1 interacts with IRSp53, which interacts with Rho GTPases to regulate the organization of the actin cytoskeleton and the pathways that regulate lamellipodia and filopodia.

NIIs are not exclusive to DRPLA; they have been found in a variety of neurodegenerative disorders. In DRPLA, NIIs have been demonstrated in both neurons and glial cells in the striatum, pontine nuclei, inferior olive, cerebellar cortex and dentate nucleus, though the incidence of neurons with NIIs is low, roughly 1-3%. In DRPLA, the NIIs are spherical, eosinophilic structures of various sizes. They are non-membrane-bound and are composed of both granular and filamentous structures. They are ubiquitinated and may be paired or in doublet form within the nucleus.

NIIs have also been demonstrated to alter the distribution of the intranuclear structures, such as promyelocytic leukemia protein (PML) nuclear bodies. Although the role of PML bodies is unclear, they are believed to be involved in apoptosis. In neurons with NII, PML bodies in DRPLA patients form a shell or ring around the ubiquitinated core. In similar polyQ diseases, the association of this PML shell has been shown to be size-dependent with larger NIIs being PML negative. This has led to two models, one in which PML bodies represent sites for NII formation and a second in which PML bodies are involved in degradation and proteolysis of NIIs.

Filementous, atrophin-1 positive, inclusions are also observed exclusively in the cytoplasm of the dentate nucleus, which are extremely similar to the inclusions observed in the motor neurons in amyotrophic lateral sclerosis.

In DRPLA, diffuse accumulation of mutant ATN1 occurs far more extensively than NII formation. The extent and frequency of neurons showing the diffuse nuclear accumulations changes depending on CAG repeat length. It is believed that the diffuse nuclear accumulations contribute to the clinical features such as dementia and epilepsy. ATN1 contains both a nuclear localization sequence and a nuclear export sequence. Cleavage of ATN1 to an N terminal fragment relieves ATN1 of its nuclear export signal and concentrates it in the nucleus. Increased nuclear concentrations have been demonstrated via transfection assay to enhance cellular toxicity.

In both the juvenile and adult forms, regions in which more than 40% of neurons became immunoreactive to 1C2 (a monoclonal antibody against expanded polyglutamine stretches) included: the nucleus basalis of Meynert, large striatal neurons, globus pallidus, subthalamic nucleus, thalamic intralaminar nucleus, lateral geniculate body, oculomotor nucleus, red nucleus, substantia nigra, trigeminal motor nucleus, nucleus raphe pontis, pontine nuclei, vestibular nucleus, inferior olive and the cerebellar dentate nucleus. The juvenile type also shows reactivity in the cerebral cortex, hippocampal CA1 area, and the reticular formation of the brainstem. Nuclei containing accumulations of mutant atrophin-1 are deformed with nuclear membrane indentations.

Diagnosis of DRPLA rests of positive family history, clinical findings, and genetic testing. Family history can be difficult to obtain if a relative was misdiagnosed, died young, or experiences late onset of symptoms. Other diseases in the differential diagnosis of adult-onset DRPLA include Huntington's and the spinocerebellar ataxias. For juvenile-onset, familial essential myoclonus and epilepsy (FEME), Lafora, Unverricht-Lundborg, Neuroaxonal dystrophy, Gaucher's disease, Sialidosis, and Galactosialidosis. To quantify the extent of the disease, an MRI, EEG and neuropsychological testing are recommended. Seizures are treated with anticonvulsants and psychiatric disturbances with psychotropic medications.

II. NUCLEIC ACID ANALOGS

A. Analogs

The present invention contemplates the use of nucleic acid analogs NAAs that mimic single-stranded oligonucleotides in their ability to hybridize to target sequences, and in particular, to mRNAs containing expanded CAG repeats. The NAAs include molecules coupled to peptides for targeting and or stability. Two particular examples of NAAs are peptide nucleic acids and locked nucleic acids.

Peptide nucleic acids (PNAs) are nonionic DNA mimics that have outstanding potential for recognizing duplex DNA (Kaihatsu et al., 2004; Nielsen et al., 1991). PNAs can be readily synthesized and bind to complementary sequences by standard Watson-Crick base-pairing (Egholm et al., 1993), allowing them to target any sequence within the genome without the need for complex synthetic protocols or design considerations. Strand invasion of duplex DNA by PNAs is not hindered by phosphate-phosphate repulsion and is both rapid and stable (Kaihatsu et al., 2004; Nielsen et al., 1991). Applications for strand invasion by PNAs include creation of artificial primosomes (Demidov et al., 2001), inhibition of transcription (Larsen and Nielsen, 1996), activation of transcription (Mollegaard et al., 1994), and directed mutagenesis (Faruqi et al., 1998). PNAs would provide a general and potent strategy for probing the structure and function of chromosomal DNA in living systems if their remarkable strand invasion abilities could be efficiently applied inside cells.

Strand invasion by PNAs in cell-free systems is most potent at sequences that are partially single-stranded (Bentin and Nielsen, 1996; Zhang et al., 2000). Assembly of RNA polymerase and transcription factors into the pre-initiation complex on DNA induces the formation of a structure known as the open complex that contains several bases of single-stranded DNA (Holstege et al., 1997; Kahl et al., 2000). The exceptional ability of PNAs to recognize duplex DNA allows them to intercept the open complex of an actively transcribed gene without a requirement for preincubation. The open complex is formed during transcription of all genes and PNAs can be synthesized to target any transcription initiation site. Therefore, antigene PNAs that target an open complex at a promoter region within chromosomal DNA would have the potential to be general tools for controlling transcription initiation inside cells.

Inhibition of translation and bacterial growth by PNAs targeted to ribosomal RNA was demonstrated by Good & Nielsen (1998). RNA guanine quadruplex invasion with complementary and homologous PNA probes has been reported by Marin & Armitage (2005).

A locked nucleic acid (LNA), often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA. LNA nucleotides can be mixed with DNA or RNA bases in the oligonucleotide whenever desired. Such oligomers are commercially available. The locked ribose conformation enhances base stacking and backbone pre-organization. This significantly increases the thermal stability (melting temperature) of oligonucleotides (Kaur et al., 2006).

LNA nucleotides are used to increase the sensitivity and specificity of expression in DNA microarrays, FISH probes, real-time PCR probes and other molecular biology techniques based on oligonucleotides. For the in situ detection of miRNA, the use of LNA was as of 2005 the only efficient method. A triplet of LNA nucleotides surrounding a single-base mismatch site maximizes LNA probe specificity unless the probe contains the guanine base of G-T mismatch (You et al., 2006).

Other oligonucleotide modifications can be made to produce NAAs. For example, stability against nuclease degradation has been achieved by introducing a phosphorothioate (P=S) backbone linkage at the 3' end for exonuclease resistance and 2' modifications (2'-OMe, 2'-F and related) for endonuclease resistance (WO 2005115481; Li et al., 2005; Choung et al., 2006). A motif having entirely of 2'-O-methyl and 2'-fluoro nucleotides has shown enhanced plasma stability and increased in vitro potency (Allerson et al., 2005). The incorporation of 2'-O-Me and 2'-O-MOE does not have a notable effect on activity (Prakash et al., 2005).

Sequences containing a 4'-thioribose modification have been shown to have a stability 600 times greater than that of natural RNA (Hoshika et al, 2004). Crystal structure studies reveal that 4'-thioriboses adopt conformations very similar to the C3'-endo pucker observed for unmodified sugars in the native duplex (Haeberli et al., 2005). Stretches of 4'-thio-RNA were well tolerated in both the guide and nonguide strands. However, optimization of both the number and the placement of 4'-thioribonucleosides is necessary for maximal potency.

In the boranophosphate linkage, a non-bridging phosphodiester oxygen is replaced by an isoelectronic borane (BH3-) moiety. Boranophosphate siRNAs have been synthesized by enzymatic routes using T7 RNA polymerase and a boranophosphate ribonucleoside triphosphate in the transcription reaction. Boranophosphate siRNAs are more active than native siRNAs if the center of the guide strand is not modified, and they may be at least ten times more nuclease resistant than unmodified siRNAs (Hall et al., 2004; Hall et al., 2006).

Certain terminal conjugates have been reported to improve or direct cellular uptake. For example, NAAs conjugated with cholesterol improve in vitro and in vivo cell permeation in liver cells (Rand et al., 2005). Soutschek et al. (2004) have reported on the use of chemically-stabilized and cholesterol-conjugated siRNAs have markedly improved pharmacological properties in vitro and in vivo. Chemically-stabilized siRNAs with partial phosphorothioate backbone and 2'-O-methyl sugar modifications on the sense and antisense strands (discussed above) showed significantly enhanced resistance towards degradation by exo- and endonucleases in serum and in tissue homogenates, and the conjugation of cholesterol to the 3' end of the sense strand of an NAA by means of a pyrrolidine linker does not result in a significant loss of gene-silencing activity in cell culture. These study demonstrates that cholesterol conjugation significantly improves in vivo pharmacological properties of NAAs.

LNA bases may be included in a DNA backbone, by they can also be in a backbone of LNA, 2'-O-methyl RNA, 2'-methoxyethyl RNA, or 2'-fluoro RNA. These molecules may utilize either a phosphodiester or phosphorothioate backbone.

U.S. Patent Publication 2008/0015162, incorporated herein by reference, provide additional examples of nucleic acid analogs useful in the present invention. The following excerpts are derived from that document and are exemplary in nature only:

In certain embodiments, oligomeric compounds comprise one or more modified monomers, including 2'-modified sugars, such as BNA's and monomers (e.g., nucleosides and nucleotides) with 2'-substituents such as allyl, amino, azido, thio, O-allyl, O—$C_1$-$C_{10}$ alkyl, —$OCF_3$, O—$(CH_2)_2$—O—$CH_3$, 2'-O$(CH_2)_2$S$CH_3$, O—$(CH_2)_2$—O—N$(R_m)(R_n)$, or O—$CH_2$—C(=O)—N$(R_m)(R_n)$, where each $R_m$ and $R_n$ is, independently, H or substituted or unsubstituted $C_1$-$C_{10}$ alkyl.

In certain embodiments, the oligomeric compounds including, but no limited to short antisense compounds of the present invention, comprise one or more high affinity monomers provided that the oligomeric compound does not comprise a nucleotide comprising a 2'-O$(CH_2)_n$H, wherein n is one to six. In certain embodiments, the oligomeric compounds including, but no limited to short antisense compounds of the present invention, comprise one or more high affinity monomer provided that the oligomeric compound does not comprise a nucleotide comprising a 2'-$OCH_3$ or a 2'-O$(CH_2)_2OCH_3$. In certain embodiments, the oligomeric compounds including, but no limited to short antisense compounds of the present invention, comprise one or more high affinity monomer provided that the oligomeric compound does not comprise a .alpha.-L-Methyleneoxy (4'-$CH_2$—O-2') BNA. In certain embodiments, the oligomeric compounds including, but no limited to short antisense compounds of the present invention, comprise one or more high affinity monomer provided that the oligomeric compound does not comprise a β-D-Methyleneoxy (4'-$CH_2$—O-2') BNA. In certain embodiments, the oligomeric compounds including, but no limited to short antisense compounds of the present invention, comprise one or more high affinity monomer provided that the oligomeric compound does not comprise a α-L-Methyleneoxy (4'-$CH_2$—O-2') BNA or a β-D-Methyleneoxy (4'-$CH_2$—O-2') BNA.

The naturally occurring base portion of a nucleoside is typically a heterocyclic base. The two most common classes of such heterocyclic bases are the purines and the pyrimidines. For those nucleosides that include a pentofuranosyl sugar, a phosphate group can be linked to the 2', 3' or 5' hydroxyl moiety of the sugar. In forming oligonucleotides, those phosphate groups covalently link adjacent nucleosides to one another to form a linear polymeric compound. Within oligonucleotides, the phosphate groups are commonly referred to as forming the internucleotide backbone of the oligonucleotide. The naturally occurring linkage or backbone of RNA and of DNA is a 3' to 5' phosphodiester linkage.

In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable with the compounds described herein. In certain embodiments, a modified nucleobase is a nucleobase that is fairly similar in structure to the parent nucleobase, such as for example a 7-deaza purine, a 5-methyl cytosine, or a G-clamp. In certain embodiments, nucleobase mimetic include more complicated structures, such as for example a tricyclic phenoxazine nucleobase mimetic. Methods for preparation of the above noted modified nucleobases are well known to those skilled in the art.

Oligomeric compounds provided herein may comprise one or more monomer, including a nucleoside or nucleotide, having a modified sugar moiety. For example, the furanosyl sugar ring of a nucleoside can be modified in a number of ways including, but not limited to, addition of a substituent group, bridging of two non-geminal ring atoms to form a bicyclic nucleic acid (BNA).

In certain embodiments, oligomeric compounds comprise one or more monomers that is a BNA. In certain such embodiments, BNAs include, but are not limited to, (A) α-L-Methyleneoxy (4'-CH$_2$—O-2') BNA, (B) β-D-Methyleneoxy (4'-CH$_2$—O-2') BNA, (C) Ethyleneoxy (4'-(CH$_2$)$_2$—O-2') BNA, (D) Aminooxy (4'-CH$_2$—O—N(R)-2') BNA and (E) Oxyamino (4'-CH$_2$—N(R)—O-2') BNA.

In certain embodiments, BNA compounds include, but are not limited to, compounds having at least one bridge between the 4' and the 2' position of the sugar wherein each of the bridges independently comprises 1 or from 2 to 4 linked groups independently selected from —[C(R$_1$)(R$_2$)]$_n$—, —C(R$_1$)=C(R$_2$)—, —C(R$_1$)=N—, —C(=NR$_1$)—, —C(=O)—, —C(=S)—, —O—, —Si(R$_1$)$_2$—, —S(=O)$_x$— and —N(R$_1$)—; wherein: x is 0, 1, or 2; n is 1, 2, 3, or 4; each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl; substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In one embodiment, each of the bridges of the BNA compounds is, independently, —[C(R$_1$)(R$_2$)]$_n$—, —[C(R$_1$)(R$_2$)]$_n$—O—, —C(R$_1$R$_2$)—N(R$_1$)—O— or —C(R$_1$R$_2$)—O—N(R$_1$)—. In another embodiment, each of said bridges is, independently, 4'-CH$_2$-2',4'-(CH$_2$)$_2$-2',4'-(CH$_2$)$_3$-2',4'-CH$_2$—O-2',4'-(CH$_2$)$_2$—O-2% 4'-CH$_2$—O—N(R$_1$)-2' and 4'-CH$_2$—N(R$_1$)—O-2'-wherein each R$_1$ is, independently, H, a protecting group or C$_1$-C$_{12}$ alkyl.

Certain BNA's have been prepared and disclosed in the patent literature as well as in scientific literature (Singh et al., 1998; Koshkin et al., 1998; Wahlestedt et al., 2000; Kumar et al., 1998; WO 94/14226; WO 2005/021570; Singh et al., 1998. Examples of issued US patents and published applications that disclose BNA s include, for example, U.S. Pat. Nos. 7,053,207; 6,268,490; 6,770,748; 6,794,499; 7,034,133; and 6,525,191; and U.S. Patent Publication Nos. 2004/0171570; 2004/0219565; 2004/0014959; 2003/0207841; 2004/0143114; and 2003/0082807.

Also provided herein are BNAs in which the 2'-hydroxyl group of the ribosyl sugar ring is linked to the 4' carbon atom of the sugar ring thereby forming a methyleneoxy (4'-CH$_2$—O-2') linkage to form the bicyclic sugar moiety (reviewed in Elayadi et al., 2001; Braasch et al., 2001; and Orum et al., 2001; see also U.S. Pat. Nos. 6,268,490 and 6,670,461). The linkage can be a methylene (—CH$_2$—) group bridging the 2' oxygen atom and the 4' carbon atom, for which the term methyleneoxy (4'-CH$_2$—O-2')

BNA is used for the bicyclic moiety; in the case of an ethylene group in this position, the term ethyleneoxy (4'-CH$_2$CH$_2$—O-2') BNA is used (Singh et al., 1998; Morita et al., 2003). Methyleneoxy (4'-CH$_2$—O-2') BNA and other bicyclic sugar analogs display very high duplex thermal stabilities with complementary DNA and RNA (Tm=+3 to +10° C.), stability towards 3'-exonucleolytic degradation and good solubility properties. Potent and nontoxic antisense oligonucleotides comprising BNAs have been described (Wahlestedt et al., 2000).

An isomer of methyleneoxy (4'-CH$_2$—O-2') BNA that has also been discussed is α-L-methyleneoxy (4'-CH$_2$—O-2') BNA which has been shown to have superior stability against a 3'-exonuclease. The α-L-methyleneoxy (4'-CH$_2$—O-2') BNA's were incorporated into antisense gapmers and chimeras that showed potent antisense activity (Frieden et al., 2003).

The synthesis and preparation of the methyleneoxy (4'-CH$_2$—O-2') BNA monomers adenine, cytosine, guanine, 5-methyl-cytosine, thymine and uracil, along with their oligomerization, and nucleic acid recognition properties have been described (Koshkin et al., 1998). BNAs and preparation thereof are also described in WO 98/39352 and WO 99/14226.

Analogs of methyleneoxy (4'-CH$_2$—O-2') BNA, phosphorothioate-methyleneoxy (4'-CH$_2$—O-2') BNA and 2'-thio-BNAs, have also been prepared (Kumar et al., 1998). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., 1998). In addition, 2'-amino- and 2'-methylamino-BNA's have been prepared and the thermal stability of their duplexes with complementary RNA and DNA strands has been previously reported.

Modified sugar moieties are well known and can be used to alter, typically increase, the affinity of the antisense compound for its target and/or increase nuclease resistance. A representative list of preferred modified sugars includes but is not limited to bicyclic modified sugars (BNA's), including methyleneoxy (4'-CH$_2$—O-2') BNA and ethyleneoxy (4'-(CH$_2$)$_2$—O-2' bridge) BNA; substituted sugars, especially 2'-substituted sugars having a 2'-F, 2'-OCH$_3$ or a 2'-O(CH$_2$)$_2$—OCH$_3$ substituent group; and 4'-thio modified sugars. Sugars can also be replaced with sugar mimetic groups among others. Methods for the preparations of modified sugars are well known to those skilled in the art. Some representative patents and publications that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,531,584; and 6,600,032; and WO 2005/121371.

In one embodiment, each of the substituted groups, is, independently, mono- or poly-substituted with optionally protected substituent groups independently selected from halogen, oxo, hydroxyl, OJ$_1$, NJ$_1$J$_2$, SJ$_1$, N$_3$, OC(=X)J$_1$, OC(=X)NJ$_1$J$_2$, NJ$_3$C(=X)NJ$_1$J$_2$ and CN, wherein each J$_1$, J$_2$ and J$_3$ is, independently, H or C$_1$-C$_6$ alkyl, and X is O, S or NJ$_1$.

In certain such embodiments, each of the substituted groups, is, independently, mono or poly substituted with substituent groups independently selected from halogen, oxo, hydroxyl, $OJ_1$, $NJ_1J_2$, $SJ_1$, $N_3$, $OC(=X)J_1$, and $NJ_3C(=X)NJ_1J_2$, wherein each $J_1$, $J_2$ and $J_3$ is, independently, H, $C_1$-$C_6$ alkyl, or substituted $C_1$-$C_6$ alkyl and X is O or $NJ_1$.

In one embodiment, each of the substituted groups, is, independently, mono or poly substituted with optionally protected substituent groups independently selected from halogen, oxo, hydroxyl, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In one embodiment, each of the substituted groups, is, independently, mono- or poly-substituted with substituent groups independently selected from halogen, oxo, hydroxyl, $OJ_1$, $NJ_1J_2$, $SJ_1$, $N_3$, $OC(=X)J_1$, and $NJ_3C(=X)NJ_1J_2$, wherein each $J_1$, $J_2$ and $J_3$ is, independently, H or $C_1$-$C_6$ alkyl, and X is O or $NJ_1$.

In certain embodiments, monomers include sugar mimetics. In certain such embodiments, a mimetic is used in place of the sugar or sugar-internucleoside linkage combination, and the nucleobase is maintained for hybridization to a selected target. Representative examples of a sugar mimetics include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., 2000, incorporated herein by reference). Methods of synthesis of sugar, nucleoside and nucleobase mimetics are well known to those skilled in the art.

Described herein are linking groups that link monomers (including, but not limited to, modified and unmodified nucleosides and nucleotides) together, thereby forming an oligomeric compound. The two main classes of linking groups are defined by the presence or absence of a phosphorus atom. Representative phosphorus containing linkages include, but are not limited to, phosphodiesters (P=O), phosphotriesters, methylphosphonates, phosphoramidate, and phosphorothioates (P=S). Representative non-phosphorus containing linking groups include, but are not limited to, methylenemethylimino (—$CH_2$—N($CH_3$)—O—$CH_2$—), thiodiester (—O—C(O)—S—), thionocarbamate (—O—C(O)(NH)—S—); siloxane (—O—Si(H)$_2$—O—); and N,N'-dimethylhydrazine (—$CH_2$—N($CH_3$)—N($CH_3$)—). Oligomeric compounds having non-phosphorus linking groups are referred to as oligonucleosides. Modified linkages, compared to natural phosphodiester linkages, can be used to alter, typically increase, nuclease resistance of the oligomeric compound. In certain embodiments, linkages having a chiral atom can be prepared a racemic mixtures, as separate enantiomers. Representative chiral linkages include, but are not limited to, alkylphosphonates and phosphorothioates. Methods of preparation of phosphorous-containing and non-phosphorous-containing linkages are well known to those skilled in the art.

The oligomeric compounds described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids et al. Included in the antisense compounds provided herein are all such possible isomers, as well as their racemic and optically pure forms.

In certain embodiments, provided herein are oligomeric compounds having reactive phosphorus groups useful for forming linkages including for example phosphodiester and phosphorothioate internucleoside linkages. Methods of preparation and/or purification of precursors or oligomeric compounds are not a limitation of the compositions or methods provided herein. Methods for synthesis and purification of oligomeric compounds including DNA, RNA, oligonucleotides, oligonucleosides, and antisense compounds are well known to those skilled in the art.

Generally, oligomeric compounds comprise a plurality of monomeric subunits linked together by linking groups. Non-limiting examples of oligomeric compounds include primers, probes, antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound.

In certain embodiments, the present invention provides chimeric oligomeric compounds. In certain such embodiments, chimeric oligomeric compounds are chimeric oligonucleotides. In certain such embodiments, the chimeric oligonucleotides comprise differently modified nucleotides. In certain embodiments, chimeric oligonucleotides are mixed-backbone antisense oligonucleotides. In general, a chimeric oligomeric compound will have modified nucleosides that can be in isolated positions or grouped together in regions that will define a particular motif. Any combination of modifications and/or mimetic groups can comprise a chimeric oligomeric compound as described herein. In certain embodiments, chimeric oligomeric compounds typically comprise at least one region modified so as to confer increased resistance to nuclease degradation, increased cellular uptake, and/or increased binding affinity for the target nucleic acid. In certain embodiments, an additional region of the oligomeric compound may serve as a substrate for enzymes capable of cleaving RNA:DNA or RNA:RNA hybrids. By way of example, RNase H is a cellular endonuclease that cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

B. Design Considerations

The present invention contemplates the production of inhibitory NAAs targeting CAG repeats of various disease-related genes and messages. In general, the NAAs will comprise a single-stranded analog of about 7-30 bases that binds to a CAG/CUG repeat, or to both a repeat and portion of a region flanking a CAG/CUG repeat, defined as "a repeat junction." The length may be 7, 8, 9, 10, 11, 12, 13, 14, 15, 16, 17, 18, 19, 20, 21, 22, 23, 24, 25, 26, 27, 28, 29 or 30 bases in length. In addition, nucleic acid analog can be designed to lack bases that recruit RNAseH.

III. TREATMENT OF REPEAT-ASSOCIATED DISEASES

The present invention also involves the treatment of polyglutamine neurodegenerative diseases, discussed above. By treatment, it is not necessary that all symptoms of the disease be addressed, or that any degree of "cure" be achieved. Rather, to accomplish a meaningful treatment, all that is required is that one or more symptoms of the disease be ameliorated to some degree, an advantageous effect be provided in combination with another therapy, or that the disease progression be slowed.

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals. One will generally desire to employ appropriate salts, buffers, and lipids to render delivery of the oligonucleotides to allow for uptake by target cells. Such methods an compositions are well known in the art, for example, as disclosed in U.S. Pat. Nos. 6,747,014 and 6,753,423. Compositions of the present invention comprise an effective amount of the oligonucleotide to cells, dissolved or dispersed in a pharmaceutically acceptable carrier or medium.

The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and anti-fungal agents, isotonic and absorption delaying agents, liposomes, cationic lipid formulations, microbubble nanoparticles, and the like. The use of such media and agents for pharmaceutically active substances is well-known in the art. I'm not so sure this is true. Delivery is a major issue in the field. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, or topical. Alternatively, administration may be by intradermal, subcutaneous, intramuscular, intraperitoneal or intravenous injection, or introduction into the CNS, such as into spinal fluid. Such compositions would normally be administered as pharmaceutically acceptable compositions, described supra.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, lipids, nanoparticles, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the NAAs of the present invention may be incorporated with excipients. The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Of particular interest to the present invention is the use of lipid delivery vehicles. Lipid vehicles encompass micelles, microemulsions, macroemulsions, liposomes, and similar carriers. The term micelles refers to colloidal aggregates of amphipathic (surfactant) molecules that are formed at a well-defined concentration known as the critical micelle concentration. Micelles are oriented with the nonpolar portions at the interior and the polar portions at the exterior surface, exposed to water. The typical number of aggregated molecules in a micelle (aggregation number) is 50 to 100. Microemulsions are essentially swollen micelles, although not all micellar solutions can be swollen to form microemulsions. Microemulsions are thermodynamically stable, are formed spontaneously, and contain particles that are extremely small. Droplet diameters in microemulsions typically range from 10 100 nm. In contrast, the term macroemulsions refers to droplets with diameters greater than 100 nm. Liposomes are closed lipid vesicles comprising lipid bilayers that encircle aqueous interiors. Liposomes typically have diameters of 25 nm to 1 μm (see, e.g., Shah, 1998; Janoff, 1999).

In one embodiment of a liposome formulation, the principal lipid of the vehicle may be phosphatidylcholine. Other useful lipids include various natural (e.g., tissue derived L-α-phosphatidyl: egg yolk, heart, brain, liver, soybean) and/or synthetic (e.g., saturated and unsaturated 1,2-diacyl-SN-glycero-3-phosphocholines, 1-acyl-2-acyl-SN-glycero-3-phosphocholines, 1,2-diheptanoyl-SN-glycero-3-phosphocholine) derivatives of the same. Such lipids can be used alone, or in combination with a secondary lipid. Such secondary helper lipids may be non-ionic or uncharged at physiological pH, including non-ionic lipids such as cholesterol and DOPE (1,2-dioleolylglyceryl phosphatidylethanolamine). The molar ratio of a phospholipid to helper lipid can range from about 3:1 to about 1:1, from about 1.5:1 to about 1:1, and about 1:1.

Another specific lipid formulation comprises the SNALP formulation, containing the lipids 3-N-[(ω methoxypoly(ethylene glycol)$_{2000}$) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar % ratio. See Zimmerman et al. (2006).

A liposome is, in simplest form, composed of two lipid layers. The lipid layer may be a monolayer, or may be multilamellar and include multiple layers. Constituents of the liposome may include, for example, phosphatidylcholine, cholesterol, phosphatidylethanolamine, etc. Phosphatidic acid, which imparts an electric charge, may also be added. Exemplary amounts of these constituents used for the production of the liposome include, for instance, 0.3 to 1 mol, 0.4 to 0.6 mol of cholesterol; 0.01 to 0.2 mol, 0.02 to 0.1 mol of phosphatidylethanolamine; 0.0 to 0.4 mol, or 0-0.15 mol of phosphatidic acid per 1 mol of phosphatidylcholine.

Liposomes can be constructed by well-known techniques (see, e.g., Gregoriadis (1993). Lipids are typically dissolved in chloroform and spread in a thin film over the surface of a tube or flask by rotary evaporation. If liposomes comprised of a mixture of lipids are desired, the individual components are mixed in the original chloroform solution. After the organic solvent has been eliminated, a phase consisting of water optionally containing buffer and/or electrolyte is added and the vessel agitated to suspend the lipid. Optionally, the suspension is then subjected to ultrasound, either in an ultrasonic bath or with a probe sonicator, until the particles are reduced in size and the suspension is of the desired clarity. For transfection, the aqueous phase is typically distilled water and the suspension is sonicated until nearly clear, which requires several minutes depending upon conditions, kind, and quality of the sonicator. Commonly, lipid concentrations are 1 mg/ml of aqueous phase, but could be higher or lower by about a factor of ten.

Lipids, from which the solvents have been removed, can be emulsified by the use of a homogenizer, lyophilized, and melted to obtain multilamellar liposomes. Alternatively, unilamellar liposomes can be produced by the reverse phase evaporation method (Szoka and Papahadjopoulos, 1978). Unilamellar vesicles can also be prepared by sonication or extrusion. Sonication is generally performed with a bath-type sonifer, such as a Branson tip sonifier (G. Heinemann Ultrashall and Labortechnik, Schwabisch Gmund, Germany) at a controlled temperature as determined by the melting point of the lipid. Extrusion may be carried out by biomembrane extruders, such as the Lipex Biomembrane Extruder (Northern Lipids Inc, Vancouver, British Columbia, Canada). Defined pore size in the extrusion filters may generate unilamellar liposomal vesicles of specific sizes. The liposomes can also be formed by extrusion through an asymmetric ceramic filter, such as a Ceraflow Microfilter (commercially available from the Norton Company, Worcester, Mass.).

Following liposome preparation, the liposomes that have not been sized during formation may be sized by extrusion to achieve a desired size range and relatively narrow distribution of liposome sizes. A size range of about 0.2-0.4 microns will allow the liposome suspension to be sterilized by filtration through a conventional filter (e.g., a 0.22 micron filter). The filter sterilization method can be carried out on a high throughput basis.

Several techniques are available for sizing liposomes to a desired size, including, ultrasonication, high-speed homogenization, and pressure filtration (Hope et al., 1985; U.S. Pat. Nos. 4,529,561 and 4,737,323). Sonicating a liposome suspension either by bath or probe sonication produces a progressive size reduction down to small unilamellar vesicles less than about 0.05 microns in size. Multilamellar vesicles can be recirculated through a standard emulsion homogenizer until selected liposome sizes, typically between about 0.1 and 0.5 microns. The size of the liposomal vesicles may be determined by quasi-elastic light scattering (QELS) (see Bloomfield, 1981). Average liposome diameter may be reduced by sonication of formed liposomes. Intermittent sonication cycles may be alternated with QELS assessment to guide efficient liposome synthesis.

Liposomes can be extruded through a small-pore polycarbonate membrane or an asymmetric ceramic membrane to yield a well-defined size distribution. Typically, a suspension is cycled through the membrane one or more times until the desired liposome size distribution is achieved. The liposomes may be extruded through successively smaller-pore membranes, to achieve a gradual reduction in liposome size. For use in the present invention, liposomes have a size of about 0.05 microns to about 0.5 microns, or having a size of about 0.05 to about 0.2 microns.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

Oligonucleotides and PNAs.

PNA-peptide conjugates were synthesized on an Expedite 8909 synthesizer (Applied Biosystems, Foster City, Calif.) using reagents obtained from Applied Biosystems (Mayfield et al., 1999; Janowski et al., 2006). PNA-peptide conjugates were purified by C-18 reversed phase HPLC and assayed by mass spectrometry (Mayfield et al., 1999; Janowski et al., 2006). LNA oligonucleotides were provided by Sigma-Proligo (Paris, France). siRNAs were purchased from Integrated DNA Technologies (IDT, Coralville, Iowa).

Cell Culture and Transfection.

Patient-derived fibroblast cell lines GM04281 and GM06151 were obtained from the Coriell Institute (Camden, N.J.). Cells were maintained at 37° C. and 5% $CO_2$ in Minimal Essential Media Eagle (MEM) (Sigma, M4655) supplemented with 10% heat inactivated fetal bovine serum (Sigma) and 0.5% MEM nonessential amino acids (Sigma). Cells were plated in E-well plates at 60,000 cells/well in supplemented MEM two days prior to transfection. Stock solutions of PNA-peptide conjugates were heated at 65° C. for 5 min before use to dissolve any aggregates that may have formed. PNA-peptide conjugates were diluted to the appropriate concentration using OptiMEM (Invitrogen, Carlsbad, Calif.) and then added to cells. After 24 h, the media containing PNA-peptides were removed and replaced by fresh supplemented MEM. Cells were typically harvested 4 days after transfection for protein assay. siRNAs or LNAs were transfected to cells using RNAiMAX (Invitrogen) according to the manufacturer's instructions. The appropriate amount of the lipid (3 µL for 100 nM oligonucleotides) were added to OptiMEM containing oligonucleotides and the oligonucleotide-lipid mixture (250 µL) were incubated for 20 min. OptiMEM was added to the mixture to a final volume of 1.25 mL and then added to cells. The media were exchanged 24 h later with fresh supplemented MEM.

Analysis of Huntingtin Expression.

Cells were harvested with trypsin-EDTA solution (Invitrogen). The protein concentration in each sample was quantified with BCA assay (Thermo Scientific, Waltham, Mass.). SDS-PAGE (separating gel: 5% acrylamide-bisacrylamide/34.7:1, 450 mM Tris-acetate pH 8.8; stacking gel: 4% acrylamide-bisacrylamide/34.7:1, 150 mM Tris-acetate pH 6.8) (XT Tricine Running Buffer, Bio-rad, Hercules, Calif.) was used to separate wild-type and mutant HTT proteins. Gels were run at 70V for 15 min followed by 100V for 4 h. The electrophoresis apparatus was placed in ice-water bath to prevent overheating of the running buffer. The inventors monitored expression of actin protein to ensure even loading on protein in each lane.

In parallel with analysis for HTT expression, portions of each protein lysate sample were analyzed for actin expression by SDS-PAGE (7.5% acrylamide pre-cast gels; Bio-Rad). These gels were run at 70V for 15 min followed by 100V for 1 h. After gel electrophoresis, proteins were transferred to membrane (Hybond-C Extra; GE Healthcare Bio-Sciences, Piscataway, N.J.). Primary antibodies specific for each protein were obtained and used at the indicated dilution ratio: anti-huntingtin antibody (MAB2166; 1:10000; Chemicon, Calif.), anti-β-actin antibody (1:10000; Sigma).

HRP conjugate anti-mouse or anti-rabbit secondary antibody (1:10000 and 1:5000, respectively; Jackson ImmunoResearch Laboratories, West Grove, Pa.) was used for visualizing proteins by SuperSignal West Pico Chemiluminescent Substrate (Thermo Scientific). Protein bands were quantified using ImageJ (Rasband, W. S., ImageJ, U.S. National Institutes of Health, Bethesda, Md., USA, rsb.info.nih.gov/ij/, 1997-2007). The percentage of inhibition was calculated as a relative value to a control sample.

Analysis of TBP, AAK1, and POU3F2.

The number of CAG repeats was estimated according to the published mRNA sequence in GeneBank. TATA box binding protein (TBP) (~19 CAG repeats, NM_003194), AAK1 (6 CAG repeats, NM_014911), and POU3F2 (~6 CAG repeats, NM_005604). Protein lysates were analyzed by SDS-PAGE (7.5% acrylamide pre-cast gels; Bio-Rad). anti-TBP antibody (1:2000; Sigma), anti-AAK1 antibody (1:1000; Abcam, Cambridge Mass.), anti-POU3F2 antibody (1:1000; Abnova, Taipei, Taiwan).

Neuronal Cells Assay (Slow et al., 2003; Tang et al., 2005).

YAC128 mice (FVBN/NJ background strain) were obtained from Jackson Labs (stock number 004938). The male YAC128 mice were crossed to wild-type (WT) female FVBN/NJ mice and P1-P2 pups were collected and genotyped by PCR. The primary cultures of striatal medium spiny neurons (MSN) were established from YAC 128 and control wild-type pups. Striata were dissected, diced and digested with trypsin. After dissociation, neurons were plated on poly-L-lysine (Sigma) coated 12 mm round coverslips (Assistent) in Neurobasal-A medium supplemented with 2% B27, 1 mM glutamine and penicillin-streptomycin (all from Invitrogen) and kept at 37° C. in a 5% $CO_2$ environment. PNA was added to the 9-DIV (days in vitro) MSN. The 13-DIV MSN were exposed for 7 h to 250 µM glutamate in Neurobasal-A added to the culture medium. Immediately after the treatment with glutamate, neurons were fixed for 30 min in 4% paraformaldehyde plus 4% sucrose in PBS (pH7.4), permeabilized for 5 min in 0.25% Triton-X-100, and stained by using the Dead-End fluorometric TUNEL System (Promega). Nuclei were counterstained with 5 µM propidium iodine (PI) (Molecular Probes). Coverslips were extensively washed with PBS and mounted in Mowiol 4-88 (Polysciences). For quantification six to eight randomly chosen microscopic fields containing 100-300 MSN each were cell-counted for YAC128 and wild-type cultures. The number of TUNEL-positive neuronal nuclei was calculated as a fraction of PI-positive neuronal nuclei in each microscopic field. The fractions of TUNEL-positive nuclei determined for each microscopic field were averaged and the results are presented as means±SE (n=number of fields counted). MSN cells were supported in culture by surrounding glial cells, but only MSN cells were counted during the neuroprotection assay.

Analysis of HTT mRNA Level by Quantitative PCR.

Total RNA from treated and untreated fibroblast cells was extracted using TRIzol (Invitrogen) 3 days after transfection. Each sample was then treated with DNase I at 25° C. for 10 min. Reverse transcription reactions were done using High Capacity Reverse Transcription Kit (Applied Biosystems) according to the manufacturer's protocol. Quantitative PCR was performed on a 7500 real-time PCR system (Applied Biosystems) using iTaq SYBR Green Supermix (Bio-rad). Data was normalized relative to levels of GAPDH mRNA.

Primer sequences specific for HTT are as follows: forward primer, 5'-CGACAGCAGTCAGTGATTG-3'; (SEQ ID NO:1) reverse primer, 5'-ACCACTCTGGCTTCACAAGG-3' (SEQ ID NO:2). Primers specific for GAPDH are obtained from Applied Biosystems.

Example 2

Results

The inventors hypothesized that it might be possible to achieve selectivity using single-stranded oligomers that discriminate among differences in mRNA secondary structure rather than mRNA primary sequence. Computational prediction, NMR and footprinting assays indicate that triplet repeat sequences within RNA form hairpin structures (FIG. 1A) (Sobczak et al., 2003; Gacy et al., 1995). The structures formed by wild-type and mutant mRNAs will possess different energies and stabilities, possibly enabling selective recognition of the mutant allele and selective inhibition of mutant protein expression.

HTT is a large protein, with a molecular weight of ~348 kDa. Unaffected individuals have up to 35 repeats, while HD patients can have from 36 to >100 repeats. The molecular weight difference between mutant and wild-type protein is no more than several kDa, complicating resolution of the proteins by SDS-PAGE. The inventors found that 5% Tris-acetate polyacrylamide gels allowed clean separation of wild-type and mutant HTT in GM04281 patient-derived fibroblast cells (wild-type allele/17 repeats, mutant allele/69 repeats) (FIG. 1B).

The inventors synthesized peptide nucleic acid (PNA)-peptide conjugates targeting HTT mRNA (Table 1; FIGS. 1C-D). PNAs are a class of DNA/RNA mimic with an uncharged amide backbone that facilitates recognition of target sequences within RNA structure (Good and Nielsen, 1998; Marin and Armitage, 2005). PNA conjugates were synthesized to contain a cationic peptide d-Lys$_8$ at the C-terminus to promote the import of PNAs into cells (Hu and Corey, 2007). REP, 5J, and 3J-8 were complementary to the CAG repeat or to the 5' or 3' junctions between the repeat and surrounding regions of the HTT gene. The inventors targeted the 3' and 5' junctions because complementarity to mRNA sequence outside the CAG repeat may further enhance the specificity for targeting mutant HTT relative to other cellular proteins. Conjugate +CTL was a positive control targeting the translation start site for HTT, while −CTL1 and −CTL2 were noncomplementary negative controls.

TABLE 1

PNA, siRNA, and LNA oligomers

| NAME | SEQUENCE | LENGTH | SEQ ID NO: |
|---|---|---|---|
| PNA-peptide conjugates: | | | |
| REP | K-GCTGCTGCTGCTGCTGCTG-K$_8$ | 19 | 3 |
| REP-N | K$_8$-GCTGCTGCTGCTGCTGCTG-K | 19 | 4 |
| REP13 | K-GCTGCTGCTGCTGCTG-K$_8$ | 16 | 5 |
| REP16 | K-GCTGCTGCTGCTG-K$_8$ | 13 | 6 |
| 5J | K-GCTGCTGCTGGAAGGACTT-K$_8$ | 19 | 7 |
| 3J-8 | K-GGCGGCTGTTGCTGCTGCT-K$_8$ | 19 | 8 |
| 3J-10 | K-CGGCTGTTGCTGCTGCTGC-K$_8$ | 19 | 9 |
| 3J-6 | K-GTGGCGGCTGTTGCTGCTG-K$_8$ | 19 | 10 |
| 3J-4 | K-CGGTGGCGGCTGTTGCTGC-K$_8$ | 19 | 11 |
| 3J-0 | K-GCGGCGGTGGCGGCTGTTG-K$_8$ | 19 | 12 |
| +CTL | K-GCTTTTCCAGGGTCGCCAT-K$_8$ | 19 | 13 |
| −CTL1 | K-GCTATACCAGCGTCGTCAT-K$_8$ | 19 | 14 |

TABLE 1-continued

PNA, siRNA, and LNA oligomers

| NAME | SEQUENCE | LENGTH | SEQ ID NO: |
|---|---|---|---|
| −CTL2 | K-ACCTACTGTCCTCGGCACCA-K$_8$ | 20 | 15 |
| 5J/ATX | K-GCTGCTGCTGTTGCTGCTT-K$_8$ | 19 | 16 |
| 3J/ATX | K-ATAGGTCCCGCTGCTGCTG-K$_8$ | 19 | 17 |
| siRNAs: | | | |
| siRNA/REP | GCUGCUGCUGCUGCUGCUGUU | 21 | 18 |
| siRNA/5J | GCUGCUGCUGGAAGGACUUUU | 21 | 19 |
| siRNA/3J | GGCGGCUGUUGCUGCUGCUUU | 21 | 20 |
| siRNA/+CTL | GCUUUUCCAGGGUCGCCAUUU | 21 | 21 |
| siRNA/−CTL1 | GCUAUACCAGCGUCGUCAUUU | 21 | 22 |
| siRNA/−CTL2 | GCAGCUGUUGCUACUGUUGTT | 21 | 23 |
| LNAs: | | | |
| LNA/REP | gcTgcTgcTgcTgcTgcTg | 19 | 24 |
| LNA/5J | gcTgcTgcTggAagGacTt | 19 | 25 |
| LNA/3J | ggCggCtgTtgCtgCtgCt | 19 | 26 |
| LNA/+CTL | gcTttTccAggGtcGccAt | 19 | 27 |
| LNA/−CTL | gcTatAccAgcGtcGtcAt | 19 | 28 |

PNAs are listed N to C terminal. siRNAs (antisense strands only and LNAs are listed 5' to 3'. D-amino acids are used in all peptide conjugates. Mismatched bases are underlined. For LNAs, modified bases are represented as capital letters and DNA bases are lower case.

PNA conjugates REP and 3J-8 inhibited expression of mutant HTT protein with IC$_{50}$ values of 0.3 µM and 1.5 µM respectively (FIG. 2A-C). Selective inhibition of mutant HTT expression by REP persisted for up to 14 days (FIG. 2D). This persistent inhibition was achieved even though treated cells went through several rounds of cell division. Addition of PNA REP did not decrease levels of HTT mRNA (FIGS. 5A-B). It is know that the binding of PNAs to mRNA does not reduce RNA levels (Knudsen and Nielsen, 1996). By contrast, the binding of PNAs to DNA blocks transcription and reduces RNA levels (Janowski et al., 2005). The finding that PNAs do not decrease RNA levels is consistent with a mechanism that involves binding to mRNA and blocking translation rather than binding to DNA and inhibition of transcription.

Many genes contain CAG repeats, including some that are essential for cellular function. At concentrations sufficient for selective inhibition of mutant HTT, addition of PNA conjugate REP did not affect expression of representative CAG repeat-containing genes including TATA box binding protein (TBP), AAK1, and POU3F2 (FIG. 2E) and did not cause cellular toxicity or affect rates of cell proliferation.

To test the consequences of selectively inhibiting expression of mutant HTT protein on phenotypes related to HD, the inventors added REP to primary neuronal cell (medium spiny striatal neurons, MSN) cultures derived from YAC128 transgenic mice (FIG. 6; FIG. 2F) (Slow et al., 2003; Tang et al., 2005). In this model, full length human HTT mRNA containing 128 CAG repeats is expressed under control of its endogenous promoter in mice that also express wild-type murine huntingtin. MSN cells expressing mutant HTT protein are more susceptible to apoptosis upon addition of glutamate (Tang et al., 2005). Following exposure to 250 µM glutamate, the fraction of apoptotic WT MSN was increased to 30-40% and the fraction of apoptotic YAC128 MSN was increased to 60-70%. Addition of REP was neuroprotective, reducing the percentage of apoptotic YAC128 cells to ~40%, similar to levels seen in wild-type MSN. Importantly, low levels of apoptotic cell death were observed in the absence of glutamate, indicating that REP is not toxic to cultured MSN cells at the concentrations used in the inventors' assay.

To examine strategies for optimizing selective inhibition of HTT expression, the inventors examined additional PNA inhibitors, duplex RNAs, and single-stranded locked nucleic acids (LNAs). They tested PNA-peptide conjugates that were 16 (REP16) and 13 (REP13) bases in length that target the CAG repeat and observed that both shorter PNAs were potent and selective inhibitors with $IC_{50}$ values of 0.4 μM and 0.5 μM respectively (FIG. 3A-B). The inventors also observed selective inhibition when the cationic peptide d-$Lys_8$ was connected to a PNA at its N- rather than the C-terminus, although switching the orientation of the peptide raised the $IC_{50}$ value to 2.5 μM (FIG. 3C). For PNAs that target sequences that systematically extend outward from the CAG repeat through the 3' junction, the efficiency of inhibition decreases as PNAs have less complementarity to the CAG repeat (FIG. 3D). These data suggest that modification strategy, PNA size, and target location affect potency of inhibition.

Duplex RNAs are currently being tested in clinical trials and have demonstrated promising features for drug development (Corey, 2007). The potency and widespread use of siRNAs makes them a good benchmark for evaluating the effectiveness of PNAs. To test whether siRNAs would also achieve selective inhibition of mutant HTT, the inventors introduced duplex RNAs analogous in sequence to PNAs REP, 5J, and 3J into GM04281 fibroblast cells. In contrast to the selective inhibition of HTT expression observed for PNAs, duplex RNAs showed little selectivity (FIGS. 7A-D).

Figure 8:
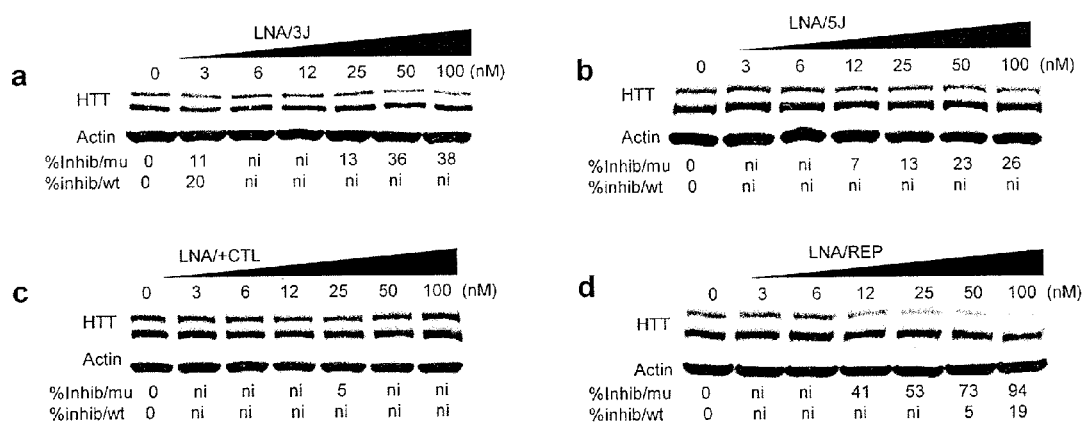
FIGS. 8A-D. Western analysis. Effect of adding increasing concentrations of LNA/3J (FIG. 8A), LNA/5J (FIG. 8B), LNA/+CTL (FIG. 8C) or LNA/REP (FIG. 8D) on HTT protein expression in GM04281 fibroblast cells. LNAs were introduced using cationic lipid.

The inventors also tested oligonucleotides that contain locked nucleic acid (LNA) bases (Vester and Wengel, 2004). LNA is an RNA analog that contains a methylene bridge between the 2' oxygen of the ribose and the 4'-carbon (FIG. 1C). This bridge reduces the conformational flexibility of the ribose and confers outstanding affinity to complementary hybridization. Unlike PNAs, LNA oligomers are being tested in clinical trials (Corey, 2007; Frieden and Orum, 2006) and this experience may help facilitate clinical development of anti-HTT oligomers. The inventors used cationic lipid to introduce LNAs into cells and observed selective inhibition of mutant HTT by LNA/REP or LNA/3J (FIG. 3D; FIG. 8). As had been observed for PNAs, concentrations of LNA that block selectively expression of mutant HTT did not affect other genes that contain CAG repeats (FIG. 3F).

HD is one of many diseases caused by an expansion of triplet repeats. Another example is spinocerebellar ataxia type 3 (Machado-Joseph Disease) (Kieling et al., 2007; Paulson, 2007; Bichelmeier et al., 2007). The disease is usually first noted in adults with patients eventually becoming wheelchair-bound or bedridden. It is one of the most common ataxias (Bichelmeier et al., 2007). The disease is caused by expanded CAG repeats (12-39 repeats are normal, beyond 45 repeats indicates disease) within the gene encoding ataxin-3. Ataxin-3 is a deubiquinating enzyme and the expanded repeat may promote protein aggregation directly by enhancing self-association of ataxin-3 and indirectly by disrupting normal proteosome processing of ataxin-3 substrates (Burnett and Pittman, 2005; Winborn et al., 2008). Interactions between the mutant RNA and cellular proteins may also contribute to the mutant phenotype (Li et al., 2008).

Figure 9:
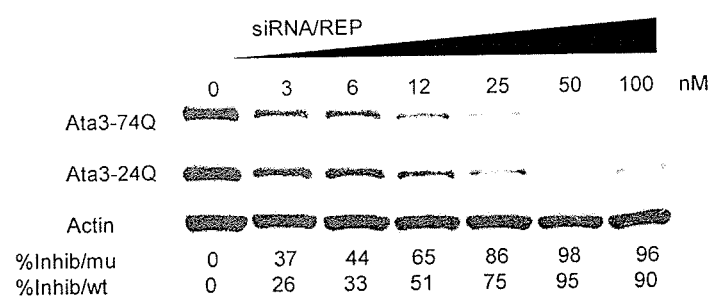
FIG. 9. Inhibition of ataxin-3 expression by siRNA/REP. Data show western analysis of protein levels in GM06151 fibroblast cells. Effect on ataxin expression of adding increasing concentrations of siRNA/REP. Duplex RNAs were introduced using cationic lipid.

The inventors obtained patient-derived cell line GM06151 that is heterozygous for an expanded CAG repeat (wild-type allele/24 repeats, mutant allele/74 repeats). The inventors tested PNA conjugates that targeted the CAG repeat region (REP and REP13), the 5' junction (5J/ATX), and the 3' junction (3J/ATX) (FIG. 4A). PNA peptide conjugates REP and REP13 that are complementary to the CAG repeat selectively inhibited mutant ataxin-3 with $IC_{50}$ values of 0.3 μM and 0.5 μM respectively (FIG. 4B-C). Conjugates that target the 3' and 5' junctions were also selective inhibitors with $IC_{50}$ values of 1.5 μM and 0.4 μM respectively (FIGS. 4D-E). These data suggest that the inventors' strategy can be extended beyond HTT to other therapeutic targets. The inventors also tested siRNA/REP. Similar to observations for inhibition of HTT protein (FIGS. 7A-D), this RNA was an effective inhibitor of ataxin-3 expression but did not selectively reduce levels of mutant protein (FIG. 9).

The inventors also directly compared PNA REP19 and LNA/REP19 with the best RNA identified by Friedlander (RNA S4) and co-workers in the GM09197 cell line used by Friedlander. This cell line has 151 CAG repeats within the mutant allele, and 21 repeats in the wild-type allele. They did not test RNA S4 in the other cell lines used for these studies because they either do not contain the polymorphism (and would therefore not be susceptible to the action of S4) or have not been characterized. Both RNA S4 and LNA/REP19 were introduced into cells using cationic lipid, permitting a direct comparison of potency.

The inventors confirmed that RNA S4 as an allele-selective inhibition of mutant HTT, with an $IC_{50}$ value of 50 nM and a maximum efficacy of 60% for inhibition of mutant HTT. No inhibition of wild-type HTT was observed (data now shown). LNA/REP19 was more potent with an $IC_{50}$ value of 4 nM for inhibition of mutant HTT and a maximum efficacy of 100% (data now shown). LNA/REP19 yielded 30% inhibition of wild-type HTT expression when 100 nM LNA was added. At concentrations of over 100 nM, the combination of lipid and RNA S4 or LNA/REP19 begins to be toxic to cells.

The inventors also tested PNAs REP19 and REP19N in GM09197 cells. Direct comparison of $IC_{50}$ values of PNA REP19 with LNA/REP19 or siRNA S4 is impossible because the PNA is delivered into cells using an attached peptide rather than cationic lipid. However quantifying inhibition allows general trends to be observed. REP19 inhibits mutant HTT with an $IC_{50}$ value of 240 nM and a selectivity of 5.4-fold relative to inhibition of wild-type HTT (data now shown). REP19N inhibits mutant HTT with an $IC_{50}$ value of 1.2 μM and little inhibition of wild-type HTT. The potencies and selectivities towards inhibition of mutant HTT in GM09197 cells are slightly better than in the other cell lines, consistent with GM09197 cells expressing HTT mRNA with a greater number of CAG repeats.

Figure 10:
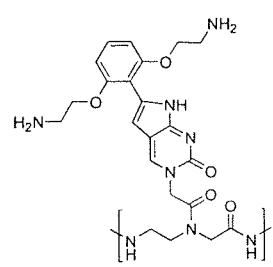
FIG. 10. Structure of [bis-o-(aminoethoxy)phenyl]pyrrolo-cytosine.

The inventors synthesized thirteen base PNAs containing one, two, three, or four PhpC (FIG. 10) substitutions (Table 2). Their sequences were complementary to the CAG repeat within HTT mRNA. All PNAs were synthesized to contain eight lysine residues in the D-configuration (D-$K_8$) to facilitate cellular uptake. Many peptides can facilitate uptake of PNAs. They chose D-$K_8$ because it was both effective and synthetically simple to add.

TABLE 2

$T_m$ data for PNA/RNA duplexes and $IC_{50}$ values for inhibition of HTT expression in fibroblast cells

| PNA Sequence | # of PhpC bases | $T_m (\Delta T_m)$ ° C. | $IC_{50}$/mut (μM) | $IC_{50}$/wt (μM) |
|---|---|---|---|---|
| I  GCTGCTGCTGCTG (SEQ ID NO: 6) | 0 | 82.9 | 0.47 ± 0.2 | >2 |
| II  GXTGCTGCTGCTG (SEQ ID NO: 31) | 1 | 84.5 (1.6) | 0.54 ± 0.05 | 1.68 ± 0.7 |
| III GCTGCTGXTGCTG (SEQ ID NO: 32) | 1 | 86.4 (3.5) | 0.71 ± 0.07 | 1.86 ± 0.1 |
| IV  GXTGCTGXTGCTG (SEQ ID NO: 33) | 2 | 83.9 (1.0) | 0.58 ± 0.05 | 1.3 ± 0.1 |
| V  GXTGXTGXTGCTG (SEQ ID NO: 34) | 3 | >87 (>4.0) | 0.97 ± 0.2 | >4 |
| VI  GXTGXTGXTGXTG (SEQ ID NO: 35) | 4 | >87 (>4.0) | 2.6 ± 0.7 | >4 |

PNAs are listed N to C terminal. All PNAs have one D-lysine at the N terminus, and eight D-lysines at the C terminus. PhpC bases (X) are underlined. $T_m$ measurements used complementary RNA oligomers. Mismatch control PNA GCCACTACT-GATA (SEQ ID NO: 36) was used for comparison.

Introduction of PhpC bases increased thermal stability (Table 2). Increases ranged for 0.5 to 1° C. per substitution and from 1 to ≥4° C. overall. The measured $T_m$ reflects base-pairing between the PNA and RNA strands and the interactions between the $D-K_8$ cationic peptide and the phosphodiester backbone of RNA.

To examine inhibition of HTT, the inventors introduced the modified PNAs into GM04281 cells. GM04281 is a patient derived fibroblast cell line with 17 CAG repeats within the wild-type allele and 69 repeats within the mutant allele. As an initial screen, the inventors tested PNAs I-VI at a concentration of 1 μM. PhpC-modified PNAs selectively inhibited HTT expression, but selectivity and/or potency appeared to decrease with the number of PhpC substitutions (FIG. 11A).

To further investigate the activity of the modified PNAs, the inventors examined inhibition of HTT expression over a range of concentrations (0-4 μM) (FIGS. 11B-F). PNA-peptide conjugate I with no PhpC substitutions was able to selectively inhibit mutant HTT expression with an $IC_{50}$ value of 0.47 μM and a >4 fold selectivity relative inhibition of the wild-type allele (Table 2) (Hu et al., 2009a). They observed that introduction of one or two PhpC bases (PNAs II, III, and IV) did not greatly affect the potency of inhibition of mutant HTT, slightly increased the potency of inhibition of wild-type HTT, and therefore did not improve selectivity. Introduction of three or four PhpC bases (PNAs V and VI) significantly decreased the potency of both mutant and wild-type HTT expression. Of the five PhpC-modified PNAs tested, triply-substituted PNA V had the best selectivity profile. Greater than 50% inhibition of mutant HTT was achieved at concentrations above 1 μM, while greater than 50% inhibition of wild-type HTT was not observed at any concentration tested.

An advantage of PhpC bases is that they are fluorescent. This property allows oligomers that contain PhpC to be tracked inside cells by fluorescent microscopy without the need to attach an additional fluorophore. Previous studies have used microscopy to track PNAs inside cells and have suggested localization to endosomes (Shiraishi et al., 2005; Kaihatsu et al., 2004; Lebleu et al., 2007; Koppelhus et al., 2008; Wolf et al., 2006; Abes et al., 2006). These studies, however, have used PNAs tagged with fluorescent groups that might alter localization. An example of how fluorescent tags can alter localization is provided by one recent study revealing that fluoroscein can redirect a ruthenium-octaarginine conjugate from endosomal to nuclear localization (Puckett and Barton, 2009). Another report noted that fluorescent dyes can alter intracellular localization of cell-penetrating peptides (Szeto et al., 2005). By using PhpC, the same oligomer can be used for both gene silencing and localization, permitting more definitive conclusions.

The inventors added doubly-modified PNA II to GM04281 cells and used confocal fluorescent microscopy to visualize uptake. Living cells were used because chemical fixation of cells can cause fluorescent compounds to spread and prevent an accurate assessment of localization (Belitsky et al., 2002). The showed that uptake of PNA II was concentrated in compartments outside the periphery of the nucleus after one day (FIG. 12A). A similar pattern of fluorescence could be observed nine days after administration of PNA conjugate to cells (FIG. 12B), even though cells double 3-4 times during this period, substantially diluting the PNA. These data suggest that PNA-peptide conjugates are long-lived but that simply allowing them to remain inside cells over long periods of time and repeated cell divisions is not sufficient to release much of the conjugate from confinement within endosomes to the cytosol.

These results have significant implications for interpretation of prior studies of PNA localization. The finding that PNAs modified with PhpC show the same intracellular distribution as PNAs modified with terminal fluorescent groups suggests that previous observations of PNA localization reflect the localization of the PNAs themselves and were not substantially influenced by the attached fluorophores.

To estimate the location of cellular uptake, the inventors treated cells with both PhpC-modified PNA and transferrin, a marker for endosomal localization. They observed that uptake of PhpC-modified PNA and transferrin were co-localized, suggesting that both largely reside in the endosome and enter cells through similar uptake mechanisms (FIGS. 12A-C). Images were obtained fifteen hours after treatment with PNA/transferrin, and some of the overlap may arise from lysosomes. Endosomal/lysosomal localization for fluorescently-labeled PNA-peptide conjugates has been reported previously (Shiraishi et al., 2005; Kaihatsu et al., 2004; Lebleu et al., 2007; Koppelhus et al., 2008; Wolf et al., 2006; Abes et al., 2006), and these results suggest that PNA conjugates containing PhpC follow a similar uptake route.

While these data indicate that most PNA is confined within endosomes, our observation of PNA-mediated inhibition demonstrates that some PNA escapes. Increasing the efficiency endosomal escape, either through addition of compounds that promote endosomal release (Shiraishi et al., 2005) or through chemical modification to the PNA (Koppelhus et al., 2008; Hu and Corey, 2007), remains a significant goal for research. The inventors also note that fluorescence is not a quantitative tool for judging the relative amount of PNA in the cytosol and endosomes because fluorescent material in the cytosol might be quenched by association with nucleic acids. The actual distribution of PNA to the cytosol may be higher than is apparent from the micrographs.

These data show that PhpC bases can increase $T_m$ values for antisense PNAs and modify their activities inside cells. The sensitivity of both $T_m$ and $IC_{50}$ values to the exact number and placement of PhpC bases emphasizes the usefulness of the modification as a tool for tailoring PNA properties.

Addition of PhpC bases to PNAs targeting the CAG repeat within HTT mRNA did not increase allele-selectivity, and in some cases reduced either potency or selectivity or both. It is not clear why modifications that increase binding affinity should decrease the potency of recognition. One possibility is the modified PNAs form stronger self-complementary interactions that compete with intermolecular binding to mRNA. This explanation is especially relevant to the sequence used in this study because it contains a triplet repeat that tends to form a self-complementary hairpin structure.

The triplet repeat within HTT mRNA is a special target. It is possible that other nucleic acid targets, such as nonrepetitive sequences chromosomal DNA or mRNA, might be more advantageous ones for recognition by PNAs modified with PhpC bases. Alternatively, the exact placement of PhpC bases may not be optimal. The inventors have previously demonstrated that attaching the D-K8 peptide to the PNA N- rather than C-termini can dramatically enhance allele-selectivity (Hu et al., 2009a; Hu et al., 2009b), and it is possible that similar simple changes in PhpC placement may also yield improved results.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. REFERENCES

The following references, to the extent that they provide exemplary procedural or other details supplementary to those set forth herein, are specifically incorporated herein by reference.

U.S. Pat. No. 4,529,561
U.S. Pat. No. 4,737,323
U.S. Pat. No. 4,981,957
U.S. Pat. No. 5,118,800
U.S. Pat. No. 5,319,080
U.S. Pat. No. 5,359,044
U.S. Pat. No. 5,393,878
U.S. Pat. No. 5,446,137
U.S. Pat. No. 5,466,786
U.S. Pat. No. 5,514,785
U.S. Pat. No. 5,519,134
U.S. Pat. No. 5,567,811
U.S. Pat. No. 5,576,427
U.S. Pat. No. 5,591,722
U.S. Pat. No. 5,597,909
U.S. Pat. No. 5,610,300
U.S. Pat. No. 5,627,053
U.S. Pat. No. 5,639,873
U.S. Pat. No. 5,646,265
U.S. Pat. No. 5,658,873
U.S. Pat. No. 5,670,633
U.S. Pat. No. 5,700,920
U.S. Pat. No. 5,792,747
U.S. Pat. No. 6,268,490
U.S. Pat. No. 6,525,191
U.S. Pat. No. 6,531,584
U.S. Pat. No. 6,600,032
U.S. Pat. No. 6,670,461
U.S. Pat. No. 6,747,014
U.S. Pat. No. 6,753,423
U.S. Pat. No. 6,770,748
U.S. Pat. No. 6,794,499
U.S. Pat. No. 7,034,133
U.S. Pat. No. 7,053,207
U.S. Patent Publn. 2003/0082807
U.S. Patent Publn. 2003/0207841
U.S. Patent Publn. 2004/0014959
U.S. Patent Publn. 2004/0143114
U.S. Patent Publn. 2004/0171570
U.S. Patent Publn. 2004/0219565
U.S. Patent Publn. 2008/0015162
Abes et al., *Controlled Release*, 110:595, 2006.
Allerson et al., *J. Med. Chem.*, 48:901-904, 2005.
Belitsky et al., *Bioorg. Med. Chem.*, 10:3313, 2002.
Bentin and Nielsen, *Biochemistry*, 35:8863-8869, 1996.
Berger et al., *Nuc Acid Res.*, 28:2911-14, 2000.
Bichelmeier et al., *J. Neuroscience*, 27:7418-7428, 2007.
Bloomfield, *Ann. Rev. Biophys. Bioeng.*, 10:421-450, 1981.
Boado et al., *J. Pharmacol. Exp. Ther.*, 295:239-243, 2002.
Borrell-Pages et al., *Cell. Mol. Life. Sci.*, 63:2642-2660, 2004.
Braasch et al., *Chem. Biol.*, 8:1-7, 2001.
Browne and Beal, *Neurochem Res.*, 29(3):531-546, 2004.
Burnett and Pittman, *Proc. Natl. Acad. Sci. USA*, 102:4330-4335, 2005.
Burnett et al., *Hum. Mol. Genet.*, 12(23):3195-3205, 2003.
Chai et al., *J. Biol. Chem.*, 279(5):3605-3611, 2004.
Choung et al., *Biochem. Biophys. Res. Commun.*, 342:919-927, 2006.
Corey, *Nat. Chem. Biol.*, 3:8-11, 2007.
Demidov et al., *Chem Biochem.*, 2:133-139, 2001.
Denovan-Wright and Davidson, *Gene Therapy*, 13:525-531, 2006.
DiFiglia et al., *Proc. Natl. Acad. Sci. USA*, 104:17204-17209, 2007.
Donaldson et al., *Curr. Biol.*, 13(3):258-262, 2003.
Dunah et al., *Science*, 296(5576):2238-2243, 2002.
Egholm et al., *Nature*, 365:566-568, 1993.
Elayadi et al., *Curr. Opinion Invens. Drugs*, 2:558-561, 2001.

Faruqi et al., *Proc. Natl. Acad. Sci. USA*, 95:398-403, 1998.
Frieden and Orum, *IDrugs*, 9:706-711, 2006.
Frieden et al., *Nucleic Acids Res.*, 21:6365-6372, 2003.
Gacy et al., *Cell*, 81:533-450, 1995.
Good and Nielsen, *Proc. Natl. Acad. Sci. USA*, 95:2073-2076, 1998.
Gregoriadis, In: *Liposome Technology*, Vols. 1-3, CRC Press, Boca Raton, Fla., 1993.
Gunawardena and Goldstein, *Arch. Neurol.*, 62(1):46-51, 2005.
Gusella and MacDonald, *Trends. Biochem. Sci.*, 31:533-540, 2006.
Haeberli et al., *Nucleic Acids Res.*, 33:3965-3975, 2005.
Hall et al., *Nucleic Acids Res.*, 32:5991-6000, 2004.
Hall et al., *Nucleic Acids Res.*, 34:2773-2781, 2006.
Harper et al., *Proc. Natl. Acad. USA*, 102:5820-5825, 2005.
Hasholt et al., *J. Gene. Med.*, 5:528-538, 2003.
Holstege et al., *EMBO J.*, 16:7468-7480, 1997.
Hope et al., *Biochim. Biophys. Acta*, 812:55-65, 1985.
Hoshika et al., *Nucleic Acids Res.*, 32:3815-3825, 2004.
Hu and Corey, Biochemistry, 46:7581-7589, 2007.
Hu et al., *Annals New York Acad. Sci.*, 2009 (in Press).
Hu et al., *Nat. Biotech.*, 27:478, 2009.
Hughes, *Curr. Biol.*, 12(4):R141-143, 2002.
Irwin et al., *J. Cell Sci.*, 118(Pt 1):233-242, 2005.
Janoff, In: *Liposomes: Rational Design*, Marcel Dekker, NY, 1999.
Janowski et al., *Nat. Chem. Biol.*, 1:210-215, 2005.
Janowski et al., *Nat. Struct. Mol. Biol.*, 13(9):787-792, 2006.
Janowski et al., *Nature Protocols*, 1:436-443, 2006.
Kahl et al., *J. Mol. Biol.*, 299:75-89, 2000.
Kaihatsu et al., *Biochemistry*, 43:14340, 2004.
Kaihatsu et al., *Chem. Biol.*, 11:749-758, 2004.
Kaur et al., *Biochemistry*, 45:7347-55, 2006.
Kazantsev et al., *Proc. Natl. Acad. Sci. USA*, 96(20):11404-11409, 1999.
Kieling et al., *Clin. Genet.*, 72:543-545, 2007.
Klement et al., *Cell*, 95(1):41-53, 1998.
Knudsen and Nielsen, *Nucl. Acid. Res.*, 24:494-500, 1996.
Koppelhus et al., *Bioconjugate Chem.*, 19:1526, 2008.
Koshkin et al., *Tetrahedron*, 54:3607-3630, 1998.
Kumar et al., *Bioorg. Med. Chem. Lett.*, 8:2219-2222, 1998.
Larsen and Nielsen, *Nucl. Acids Res.*, 24:458-463, 1996.
Lebleu et al., *Adv. Drug Deliv. Rev.*, 60:517, 2007.
Li et al., *J Biol. Chem.*, 277(31):28212-28221, 2002.
Li et al., *Nat. Med.*, 11:944-951, 2005.
Li et al., *Nature*, 453:1107-1111, 2008.
Mao et al., *Proc. Natl. Acad. Sci. USA*, 102(36):12700-12705, 2005.
Marin and Armitage, *J. Am. Chem. Soc.*, 127:8032-8033, 2005.
Mayfield and Corey, *Anal. Biochem.*, 268:401-404, 1999.
Mollegaard et al., *Proc. Natl. Acad. Sci. USA*, 91:3892-3895, 1994.
Morita et al., *Bioorganic Medicinal Chem.*, 11:2211-2226, 2003.
Nasir et al., *Cell*, 81:811-823, 1995.
Nicastro et al., *Proc. Natl. Acad. Sci. USA*, 102(30):10493-10498, 2005.
Nielsen et al., *Science*, 254:1497-1500, 1991.
Nucifora et al., *Science*, 291(5512):2423-2428, 2001.
Orum et al., *Curr. Opinion Mol. Ther.*, 3:239-243, 2001.
Paulson, *Seminars in Neurol.*, 27:133-142, 2007.
PCT Appln. WO 2005/021570
PCT Appln. WO 2005/121371
PCT Appln. WO 2005115481
PCT Appln. WO 94/14226
PCT Appln. WO 98/39352
PCT Appln. WO 99/14226
Prakash et al., *J. Med. Chem.*, 48:4247-4253, 2005.
Puckett and Barton, *J. Am. Chem. Soc.*, 131:8738, 2009.
Rand et al., *Cell*, 123:621-629, 2005.
Remington's Pharmaceutical Sciences, 15$^{th}$ ed., pages 1035-1038 and 1570-1580, Mack Publishing Company, Easton, Pa., 1980.
Rodriguez-Lebron and Paulson, *Gene Therapy*, 13:576-581, 2006.
Scheel et al., *Hum. Mol. Genet.*, 12(21):2845-2852, 2003.
Schramke et al., *Nature*, 435:1275-1279, 2005.
Schwarz et al., *PLOS Genetics*, 2:1307-1318, 2006.
Servadio et al., *Nat. Genet.*, 10(1):94-98, 1995.
Shah, In: *Micelles, Microemulsions, and Monolayers: Science and Technology*, Marcel Dekker, NY, 1998.
Shiraishi et al., *Chem. Biol.* 2005, 12, 923, 2005.
Singh et al., *Chem. Commun.*, 4:455-456, 1998.
Singh et al., *J. Org. Chem.*, 63:10035-10039, 1998.
Slow et al., *Hum. Mol. Gen.*, 12:1555-1567, 2003.
Sobczak et al., *Nucl. Acids Res.*, 31:5469-5482, 2003.
Soutschek et al., *Nature*, 432(7014):173-178, 2004.
Steffan et al., *Nature*, 413(6857):739-743, 2001.
Szeto et al., *FASEB J.*, 19:118, 2005.
Szoka and Papahadjopoulos, *Proc. Natl. Acad. Sci. USA*, 75:4194 4198, 1978.
Tang et al., *Proc. Natl. Acad. Sci. USA*, 102:2602-2607, 2005.
Vester and Wengel, *Biochemistry*, 43:13233-13241, 2004.
Wahlestedt et al., *Proc. Natl. Acad. Sci. USA*, 97:5633-5638, 2000.
Walker, Lancet, 369:218-228, 2007.
Warrick et al., *Mol. Cell*, 18(1):37-48, 2005.
White et al., *Nat. Genetics*, 17:404-410, 1997.
Winborn et al., *J. Biol. Chem.*, 2008 (In Press).
Wolf et al., *Biochemistry*, 45:14944-14954, 2006.
You et al., *Nucl. Acids Res.*, 34:e60, 2006.
Yue et al., *Hum. Mol. Genet.*, 10(1):25-30, 2001.
Zhai et al. *Cell*, 123(7):1241-53, 2005.
Zhang et al., *Nucl. Acids Res.*, 28:3332-3338, 2000.
Zimmerman et al., *Nature*, 441:111-114, 2006.

---

The invention claimed is:

1. A method for inhibiting expression of a disease protein encoded by an mRNA having expanded tri-nucleotide repeat region comprising contacting a cell that produces said disease protein with an amount of a nucleic acid analog that targets said repeat region of said mRNA, wherein (i) inhibiting is selective for said disease protein over a normal form of said disease protein, an mRNA for which lacks an expanded trinucleotide repeat region, and (ii) inhibiting does not substantially affect production of said mRNA.

2. The method of claim 1, wherein said repeat region is about 125 repeats or less in size.

3. The method of claim 2, wherein said disease protein is Huntingtin, ataxin-3, ataxin-1, ataxin-2 or atrophin1.

4. The method of claim 1, wherein said nucleic acid analog is about 7 to about 30 bases in length.

5. The method of claim 1, wherein said nucleic acid analog is a peptide-nucleic acid (PNA).

6. The method of claim 5, wherein said PNA further comprises a cationic peptide.

7. The method of claim 1, wherein said nucleic acid analog a locked nucleic acid (LNA).

8. The method of claim 7, wherein said LNA further comprises a cationic peptide.

9. The method of claim 1, wherein said nucleic acid analog further targets a repeat region junction.

10. The method of claim 1, wherein said nucleic acid analog lacks bases that recruit RNAseH.

11. A method for inhibiting expression, in a subject, of a disease protein encoded by an mRNA having expanded tri-nucleotide repeat region comprising administering to said subject an amount of a nucleic acid analog that targets said repeat region of said mRNA, wherein (i) inhibiting is selective for said disease protein over a normal form of said disease protein, an mRNA for which lacks an expanded tri-nucleotide repeat region, and (ii) inhibiting does not substantially affect production of said mRNA.

12. The method of claim 11, wherein said repeat region is about 125 repeats or less in size.

13. The method of claim 12, wherein said disease protein is Huntingtin, ataxin-3, ataxin-1, ataxin-2 or atrophin1.

14. The method of claim 11, wherein said nucleic acid analog is about 7 to about 30 bases in length.

15. The method of claim 11, wherein said nucleic acid analog is a peptide-nucleic acid (PNA).

16. The method of claim 15, wherein said PNA comprises at least one modified base.

17. The method of claim 16, wherein said modified base is [bis-o-(aminoethoxy)phenyl]pyrrolocytosine.

18. The method of claim 15, wherein said PNA further comprises a cationic peptide.

19. The method of claim 11, wherein said nucleic acid analog a locked nucleic acid (LNA).

20. The method of claim 19, wherein said LNA further comprises a cationic peptide.

21. The method of claim 11, wherein said nucleic acid analog further targets a repeat region junction.

22. The method of claim 11, wherein said nucleic acid analog lacks bases that recruit RNAseH.

23. The method of claim 11, wherein said nucleic acid analog is administered more than once.

24. The method of claim 23, wherein said nucleic acid analog is administered at least about once every week.

25. The method of claim 11, wherein said nucleic acid analog is administered orally, intravenously, intraarterially, intramuscularly or into the CNS.

26. The method of claim 11, wherein said nucleic acid analog is administered in a lipid formulation.

27. The method of claim 11, further comprising administering a second therapy to said subject.

* * * * *

SEQUENCE LISTING

<160> NUMBER OF SEQ ID NOS: 36

<210> SEQ ID NO 1
<211> LENGTH: 19
<212> TYPE: DNA
<213> ORGANISM: Artificial
<220> FEATURE:
<223> OTHER INFORMATION: Synthetic primer

<400> SEQUENCE: 1

-continued cgacagcagt cagtgattg                                              19

<210> SEQ ID NO 2
<211> LENGTH: 20
<212> TYPE: DNA
<213> ORGANISM: Artificial
<220> FEATURE:
<223> OTHER INFORMATION: Synthetic primer

<400> SEQUENCE: 2
accactctgg cttcacaagg                                             20

<210> SEQ ID NO 3
<211> LENGTH: 19
<212> TYPE: DNA
<213> ORGANISM: Artificial
<220> FEATURE:
<223> OTHER INFORMATION: Synthetic primer

<400> SEQUENCE: 3
gctgctgctg ctgctgctg                                              19

<210> SEQ ID NO 4
<211> LENGTH: 19
<212> TYPE: DNA
<213> ORGANISM: Artificial
<220> FEATURE:
<223> OTHER INFORMATION: Synthetic primer

<400> SEQUENCE: 4
gctgctgctg ctgctgctg                                              19

<210> SEQ ID NO 5
<211> LENGTH: 16
<212> TYPE: DNA
<213> ORGANISM: Artificial
<220> FEATURE:
<223> OTHER INFORMATION: Synthetic primer

<400> SEQUENCE: 5
gctgctgctg ctgctg                                                 16

<210> SEQ ID NO 6
<211> LENGTH: 13
<212> TYPE: DNA
<213> ORGANISM: Artificial
<220> FEATURE:
<223> OTHER INFORMATION: Synthetic primer

<400> SEQUENCE: 6
gctgctgctg ctg                                                    13

<210> SEQ ID NO 7
<211> LENGTH: 19
<212> TYPE: DNA
<213> ORGANISM: Artificial
<220> FEATURE:
<223> OTHER INFORMATION: Synthetic primer

<400> SEQUENCE: 7
gctgctgctg gaaggactt                                              19

<210> SEQ ID NO 8
<211> LENGTH: 19
<212> TYPE: DNA

<213> ORGANISM: Artificial
<220> FEATURE:
<223> OTHER INFORMATION: Synthetic primer

<400> SEQUENCE: 8
ggcggctgtt gctgctgct                                                    19

<210> SEQ ID NO 9
<211> LENGTH: 19
<212> TYPE: DNA
<213> ORGANISM: Artificial
<220> FEATURE:
<223> OTHER INFORMATION: Synthetic primer

<400> SEQUENCE: 9
cggctgttgc tgctgctgc                                                    19

<210> SEQ ID NO 10
<211> LENGTH: 19
<212> TYPE: DNA
<213> ORGANISM: Artificial
<220> FEATURE:
<223> OTHER INFORMATION: Synthetic primer

<400> SEQUENCE: 10
gtggcggctg ttgctgctg                                                    19

<210> SEQ ID NO 11
<211> LENGTH: 19
<212> TYPE: DNA
<213> ORGANISM: Artificial
<220> FEATURE:
<223> OTHER INFORMATION: Synthetic primer

<400> SEQUENCE: 11
cggtggcggc tgttgctgc                                                    19

<210> SEQ ID NO 12
<211> LENGTH: 19
<212> TYPE: DNA
<213> ORGANISM: Artificial
<220> FEATURE:
<223> OTHER INFORMATION: Synthetic primer

<400> SEQUENCE: 12
gcggcggtgg cggctgttg                                                    19

<210> SEQ ID NO 13
<211> LENGTH: 19
<212> TYPE: DNA
<213> ORGANISM: Artificial
<220> FEATURE:
<223> OTHER INFORMATION: Synthetic primer

<400> SEQUENCE: 13
gcttttccag ggtcgccat                                                    19

<210> SEQ ID NO 14
<211> LENGTH: 19
<212> TYPE: DNA
<213> ORGANISM: Artificial
<220> FEATURE:
<223> OTHER INFORMATION: Synthetic primer

<400> SEQUENCE: 14
gctataccag cgtcgtcat                                                    19

<210> SEQ ID NO 15
<211> LENGTH: 20
<212> TYPE: DNA
<213> ORGANISM: Artificial
<220> FEATURE:
<223> OTHER INFORMATION: Synthetic primer

<400> SEQUENCE: 15
acctactgtc ctcggcacca                                           20

<210> SEQ ID NO 16
<211> LENGTH: 19
<212> TYPE: DNA
<213> ORGANISM: Artificial
<220> FEATURE:
<223> OTHER INFORMATION: Synthetic primer

<400> SEQUENCE: 16
gctgctgctg ttgctgctt                                            19

<210> SEQ ID NO 17
<211> LENGTH: 19
<212> TYPE: DNA
<213> ORGANISM: Artificial
<220> FEATURE:
<223> OTHER INFORMATION: Synthetic primer

<400> SEQUENCE: 17
ataggtcccg ctgctgctg                                            19

<210> SEQ ID NO 18
<211> LENGTH: 21
<212> TYPE: DNA
<213> ORGANISM: Artificial
<220> FEATURE:
<223> OTHER INFORMATION: Synthetic primer

<400> SEQUENCE: 18
gcugcugcug cugcugcugt t                                         21

<210> SEQ ID NO 19
<211> LENGTH: 21
<212> TYPE: DNA
<213> ORGANISM: Artificial
<220> FEATURE:
<223> OTHER INFORMATION: Synthetic primer

<400> SEQUENCE: 19
gcugcugcug gaaggacuut t                                         21

<210> SEQ ID NO 20
<211> LENGTH: 21
<212> TYPE: DNA
<213> ORGANISM: Artificial
<220> FEATURE:
<223> OTHER INFORMATION: Synthetic primer

<400> SEQUENCE: 20
ggcggcuguu gcugcugcut t                                         21

<210> SEQ ID NO 21
<211> LENGTH: 21
<212> TYPE: DNA
<213> ORGANISM: Artificial
<220> FEATURE:

<223> OTHER INFORMATION: Synthetic primer

<400> SEQUENCE: 21
gcuuuuccag ggucgccaut t                                              21

<210> SEQ ID NO 22
<211> LENGTH: 21
<212> TYPE: DNA
<213> ORGANISM: Artificial
<220> FEATURE:
<223> OTHER INFORMATION: Synthetic primer

<400> SEQUENCE: 22
gcuauaccag cgucgucaut t                                              21

<210> SEQ ID NO 23
<211> LENGTH: 21
<212> TYPE: DNA
<213> ORGANISM: Artificial
<220> FEATURE:
<223> OTHER INFORMATION: Synthetic primer

<400> SEQUENCE: 23
gcagcuguug cuacuguugt t                                              21

<210> SEQ ID NO 24
<211> LENGTH: 19
<212> TYPE: DNA
<213> ORGANISM: Artificial
<220> FEATURE:
<223> OTHER INFORMATION: Synthetic primer

<400> SEQUENCE: 24
gctgctgctg ctgctgctg                                                 19

<210> SEQ ID NO 25
<211> LENGTH: 19
<212> TYPE: DNA
<213> ORGANISM: Artificial
<220> FEATURE:
<223> OTHER INFORMATION: Synthetic primer

<400> SEQUENCE: 25
gctgctgctg gaaggactt                                                 19

<210> SEQ ID NO 26
<211> LENGTH: 19
<212> TYPE: DNA
<213> ORGANISM: Artificial
<220> FEATURE:
<223> OTHER INFORMATION: Synthetic primer

<400> SEQUENCE: 26
ggcggctgtt gctgctgct                                                 19

<210> SEQ ID NO 27
<211> LENGTH: 19
<212> TYPE: DNA
<213> ORGANISM: Artificial
<220> FEATURE:
<223> OTHER INFORMATION: Synthetic primer

<400> SEQUENCE: 27
gcttttccag ggtcgccat                                                 19

```
<210> SEQ ID NO 28
<211> LENGTH: 19
<212> TYPE: DNA
<213> ORGANISM: Artificial
<220> FEATURE:
<223> OTHER INFORMATION: Synthetic primer

<400> SEQUENCE: 28
gctataccag cgtcgtcat                                                19

<210> SEQ ID NO 29
<211> LENGTH: 180
<212> TYPE: RNA
<213> ORGANISM: Homo sapien

<400> SEQUENCE: 29
cugccgugcc gggcgggaga ccgccauggc gacccuggaa aagcugauga aggccuucga    60
gucccucaag uccuuccagc agcagcagca gcagcagcag cagcagcagc agcagcagca   120
gcagcagcag cagcagcagc aacagccgcc accgccgccg ccgccgccgc cgccuccuca   180

<210> SEQ ID NO 30
<211> LENGTH: 120
<212> TYPE: DNA
<213> ORGANISM: Homo sapien

<400> SEQUENCE: 30
acgagaagcc tactttgaaa acagcagcaa aaagcagcaa cagcagcagc agcagcagca    60
gcagcagcag cagcagcagc agcagcagca gggggaccta tcaggacaga gttcacatcc   120

<210> SEQ ID NO 31
<211> LENGTH: 13
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (2)..(2)
<223> OTHER INFORMATION: n = PhpC

<400> SEQUENCE: 31
gntgctgctg ctg                                                      13

<210> SEQ ID NO 32
<211> LENGTH: 13
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (8)..(8)
<223> OTHER INFORMATION: n = PhpC

<400> SEQUENCE: 32
gctgctgntg ctg                                                      13

<210> SEQ ID NO 33
<211> LENGTH: 13
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (2)..(2)
```

-continued

```
<223> OTHER INFORMATION: n = PhpC
<220> FEATURE:
<221> NAME/KEY: misc_feature
<222> LOCATION: (8)..(8)
<223> OTHER INFORMATION: n = PhpC

<400> SEQUENCE: 33
gntgctgntg ctg                                                          13

<210> SEQ ID NO 34
<211> LENGTH: 13
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (2)..(2)
<223> OTHER INFORMATION: n = PhpC
<220> FEATURE:
<221> NAME/KEY: misc_feature
<222> LOCATION: (5)..(5)
<223> OTHER INFORMATION: n = PhpC
<220> FEATURE:
<221> NAME/KEY: misc_feature
<222> LOCATION: (8)..(8)
<223> OTHER INFORMATION: n = PhpC

<400> SEQUENCE: 34
gntgntgntg ctg                                                          13

<210> SEQ ID NO 35
<211> LENGTH: 13
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (2)..(2)
<223> OTHER INFORMATION: n = PhpC
<220> FEATURE:
<221> NAME/KEY: misc_feature
<222> LOCATION: (5)..(5)
<223> OTHER INFORMATION: n = PhpC
<220> FEATURE:
<221> NAME/KEY: misc_feature
<222> LOCATION: (8)..(8)
<223> OTHER INFORMATION: n = PhpC
<220> FEATURE:
<221> NAME/KEY: misc_feature
<222> LOCATION: (11)..(11)
<223> OTHER INFORMATION: n = PhpC

<400> SEQUENCE: 35
gntgntgntg ntg                                                          13

<210> SEQ ID NO 36
<211> LENGTH: 13
<212> TYPE: DNA
<213> ORGANISM: Artificial
<220> FEATURE:
<223> OTHER INFORMATION: Synthetic primer

<400> SEQUENCE: 36
gccactactg ata                                                          13
```